United States Patent
Andon et al.

(10) Patent No.: US 10,657,156 B2
(45) Date of Patent: *May 19, 2020

(54) ENERGY EXPENDITURE CALCULATION USING DATA FROM MULTIPLE DEVICES

(71) Applicant: NIKE, Inc., Beaverton, OR (US)

(72) Inventors: Christopher Andon, Portland, OR (US); Brett S. Kirby, Portland, OR (US); Bradley W. Wilkins, Beaverton, OR (US); David Clark, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 189 days.

This patent is subject to a terminal disclaimer.

(21) Appl. No.: 14/988,216

(22) Filed: Jan. 5, 2016

(65) Prior Publication Data
US 2016/0196326 A1 Jul. 7, 2016

Related U.S. Application Data

(60) Provisional application No. 62/099,851, filed on Jan. 5, 2015.

(51) Int. Cl.
*G06F 16/28* (2019.01)
*G06F 7/02* (2006.01)
(Continued)

(52) U.S. Cl.
CPC .......... *G06F 16/285* (2019.01); *A61B 5/1118* (2013.01); *A61B 5/4866* (2013.01); *G06F 7/02* (2013.01)

(58) Field of Classification Search
CPC . G06F 17/30598; G06F 16/285; A61B 5/1118
(Continued)

(56) References Cited

U.S. PATENT DOCUMENTS 3,797,010 A * 3/1974 Adler .................. A61B 5/22
340/323 R
7,690,556 B1 * 4/2010 Kahn ................... G01C 22/006
235/105
(Continued)

FOREIGN PATENT DOCUMENTS

EP 2745777 A1 6/2014
GB 2512305 A 10/2014
(Continued)

OTHER PUBLICATIONS

Apr. 12, 2016—(WO) ISR & WO—App. PCT/US16/012202.

*Primary Examiner* — Pierre M Vital
*Assistant Examiner* — Nargis Sultana
(74) *Attorney, Agent, or Firm* — Banner & Witcoff, Ltd.

(57) ABSTRACT

Aspects relate to athletic metric values from data received from different sources having different devices that employ different processes to calculate the values. Data may be received from a connected device that utilizes a first operating protocol, and be received by a device utilizing a second operating protocol. An activity metric may be identified from received data, and a determination may be made as to whether the activity metric is calculated using a best available data source. If it is determined that the received data represents a best available data source, the received data may be added to a metric database, the received data may be classified into an activity group, and an energy expenditure value may be calculated from the received data.

16 Claims, 14 Drawing Sheets

(51) Int. Cl.
*A61B 5/11* (2006.01)
*A61B 5/00* (2006.01)

(58) Field of Classification Search
USPC .......................................................... 707/740
See application file for complete search history.

(56) References Cited

U.S. PATENT DOCUMENTS

| | | | | |
|---|---|---|---|---|
| 9,643,052 B2* | 5/2017 | Tchao | ................. | G06F 19/3418 |
| 2005/0004436 A1* | 1/2005 | Nissila | ............... | A61B 5/02438 |
| | | | | 600/300 |
| 2009/0103435 A1* | 4/2009 | Celentano | ............. | H04W 28/22 |
| | | | | 370/232 |
| 2009/0149299 A1* | 6/2009 | Tchao | ................. | G06F 19/3481 |
| | | | | 482/9 |
| 2011/0003665 A1* | 1/2011 | Burton | ................... | G04G 17/04 |
| | | | | 482/9 |
| 2011/0276304 A1* | 11/2011 | Yin | ........................ | A61B 5/1118 |
| | | | | 702/141 |
| 2012/0253488 A1* | 10/2012 | Shaw | ..................... | G06Q 10/04 |
| | | | | 700/91 |
| 2012/0274508 A1* | 11/2012 | Brown | .................... | G04F 10/00 |
| | | | | 342/357.25 |
| 2013/0184613 A1* | 7/2013 | Homsi | .................... | G01P 13/00 |
| | | | | 600/595 |
| 2013/0191034 A1* | 7/2013 | Weast | ..................... | G06F 17/00 |
| | | | | 702/19 |
| 2013/0311562 A1* | 11/2013 | platt | ....................... | H04L 65/403 |
| | | | | 709/204 |
| 2014/0164611 A1* | 6/2014 | Molettiere | ............ | A61B 5/1112 |
| | | | | 709/224 |
| 2014/0244209 A1* | 8/2014 | Lee | ..................... | G06K 9/00342 |
| | | | | 702/150 |
| 2015/0057942 A1* | 2/2015 | Self | ........................ | G06F 19/00 |
| | | | | 702/19 |
| 2015/0374240 A1* | 12/2015 | Lee | ...................... | A61B 5/0205 |
| | | | | 600/483 |
| 2016/0022220 A1* | 1/2016 | Lee | ........................ | A61B 5/721 |
| | | | | 600/479 |
| 2016/0256744 A1* | 9/2016 | Rosano | ............. | A63B 71/0616 |

FOREIGN PATENT DOCUMENTS

| | | | |
|---|---|---|---|
| JP | 2014179087 A | 9/2014 | |
| WO | 2010096691 A2 | 8/2010 | |
| WO | 2010129221 A1 | 11/2010 | |
| WO | 2013082436 A1 | 6/2013 | |
| WO | WO 2013082436 A1 * | 6/2013 | ........... G01C 22/006 |
| WO | WO-2013082436 A1 * | 6/2013 | ........... G01C 22/006 |

* cited by examiner

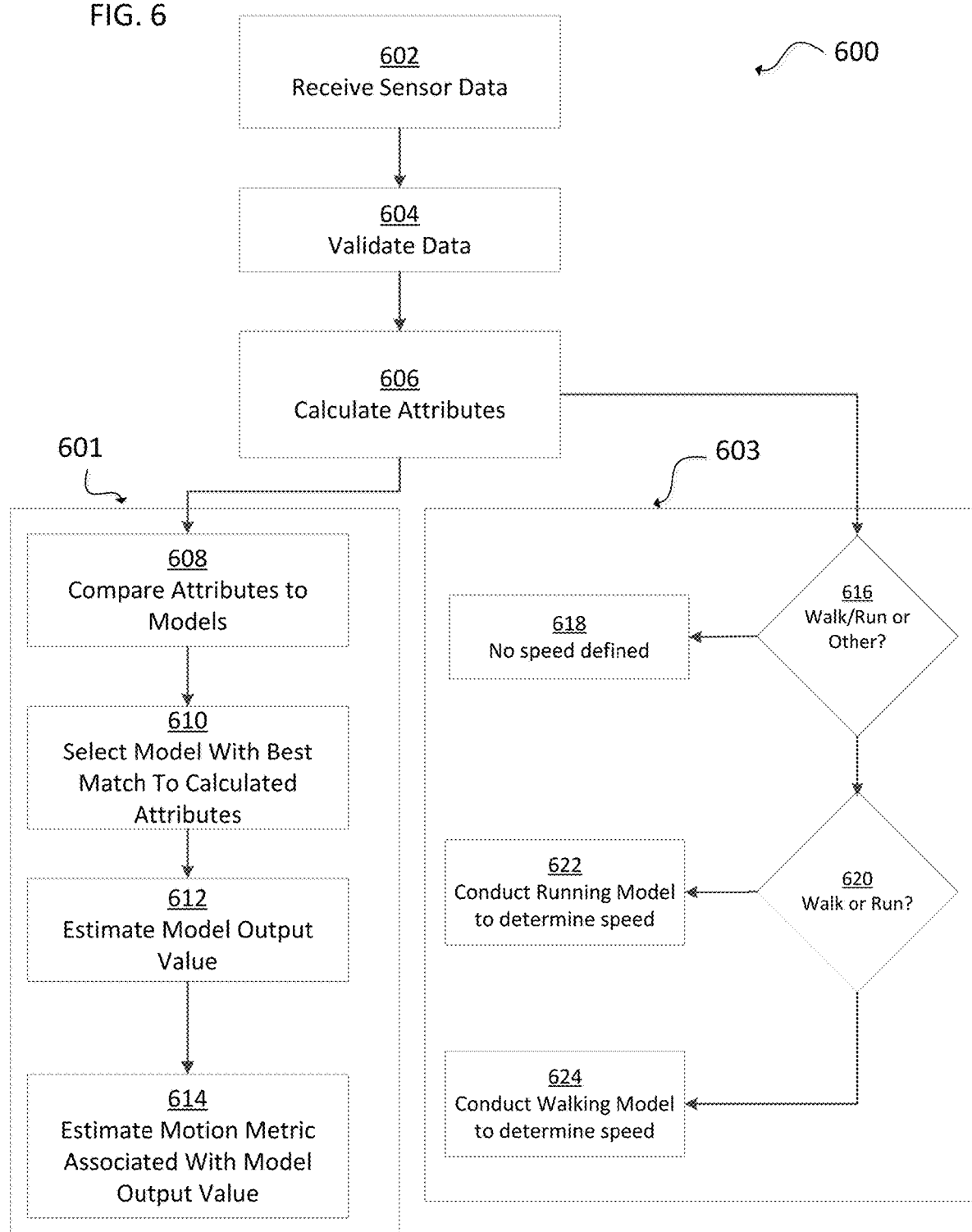

ENERGY EXPENDITURE CALCULATION USING DATA FROM MULTIPLE DEVICES

CROSS REFERENCE TO RELATED APPLICATIONS

This application claims the benefit of, and priority to, U.S. Provisional Patent Application No. 62/099,851, entitled "ENERGY EXPENDITURE CALCULATION USING DATA FROM MULTIPLE DEVICES" filed Jan. 5, 2015. The content of which is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using athletic activity services and systems.

Many existing services and devices fail to provide accurate assessment of the user's energy expenditure, such as caloric burn, during physical activity. Therefore, users are unaware of the benefits that certain activities, which may include daily routines that are often not thought of as being a "workout", are to their health. Existing devices for allowing users to monitor their energy expenditure often suffer from one or more deficiencies, including: cumbersome collection systems, inaccurate measurements that are beyond an acceptable threshold, unacceptable latency in reporting the values, erroneous classification of activities based upon detected motions of the user, failure to account for deviations between different users, improperly including repetitive behavior as being classified as a specific activity, such as for example, running and/or walking, relatively high power consumption, and/or a combination of these or other deficiencies.

Therefore, improved systems and methods to address at least one or more of these shortcomings in the art are desired.

BRIEF SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Illustrative embodiments may relate to a system, method, apparatus, and computer-readable media configured for receiving data from a connected device that utilizes a first operating protocol. In one embodiment, the data may be received by a processor that utilizes a second operating protocol. Further, an activity metric may be identified from the received data. In certain embodiments, the identified activity metric may be compared to a metric database to determine whether a best available source of data is used to calculate the activity metric. If the activity metric is calculated from a best available data source, the received data may be added to a metric database, the received data may be classified into an activity group, and an energy expenditure for a user may be calculated from one or more stored activity metrics.

In one embodiment, an activity being performed by a user is identified based upon the user input of an activity classification.

Another illustrative embodiment may relate to a system, method, apparatus, and computer-readable media configured for receiving data from a connected device that utilizes a first operating protocol. In one embodiment, the data may be received by a processor that utilizes a second operating protocol. Further, an activity metric may be identified from the received data. In certain embodiments, the identified activity metric may be compared to a metric database to determine whether the best available source of data is used to calculate the activity metric. If the activity metric is calculated from the best available data source, the received data may be added to the metric database, the received data may be classified into an activity group, a confidence weighting may be associated with the activity metric, an energy expenditure value for a user may be calculated from one or more stored activity metrics, and a confidence value may be calculated and associated with the calculated energy expenditure value.

Yet another illustrative embodiment may relate to a system, method, apparatus, and computer-readable media configured for calculating a final cumulative athletic metric based upon a user's movements during a first time frame. In certain embodiments, the first time frame may comprise a first and a second time period. Further, in certain embodiments, first and second values may be received from first and second sources that represent athletic metrics resulting from processes conducted on first and second devices. The first value may be associated with a modification scalar based on the first source and the first device. Further, a normalizing factor may be used to normalize data from the first source and the second source. Additionally, a cumulative normalized athletic metric may be calculated using an adjusted first value and an adjusted second value.

BRIEF DESCRIPTION OF THE DRAWINGS

FIG. 6 shows an example flowchart that may be implemented to calculate metrics, including energy expenditure and speed.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
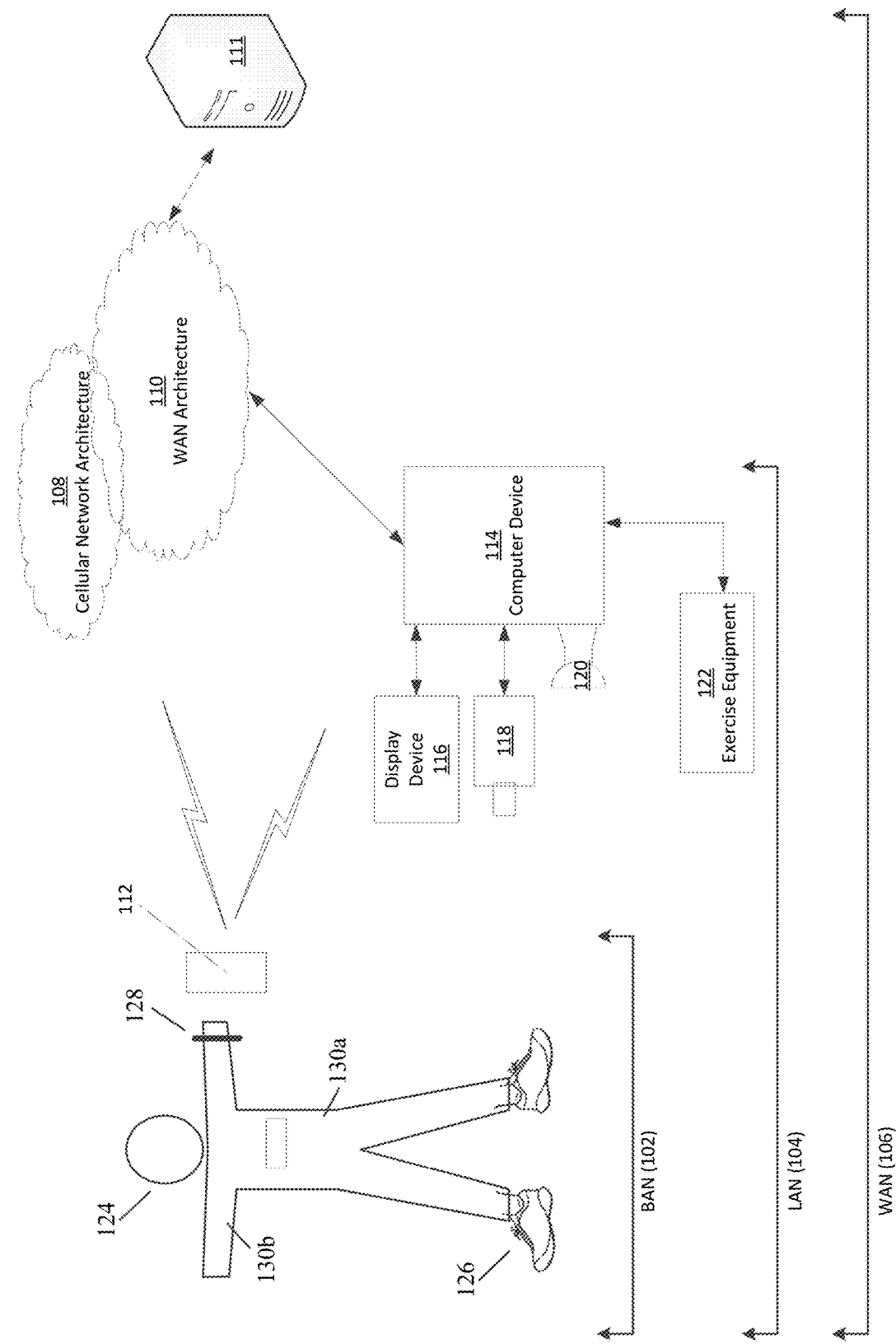
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
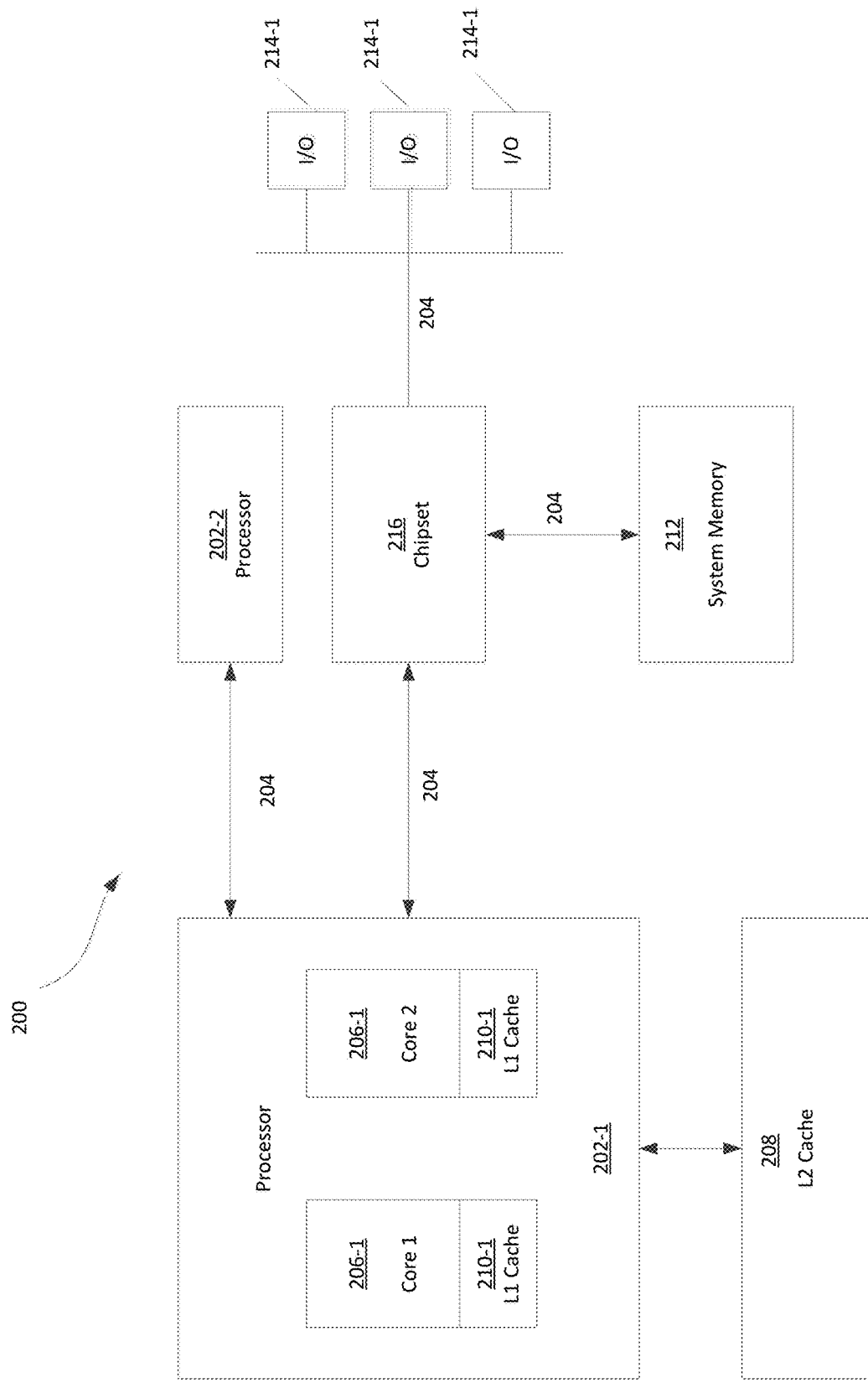
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
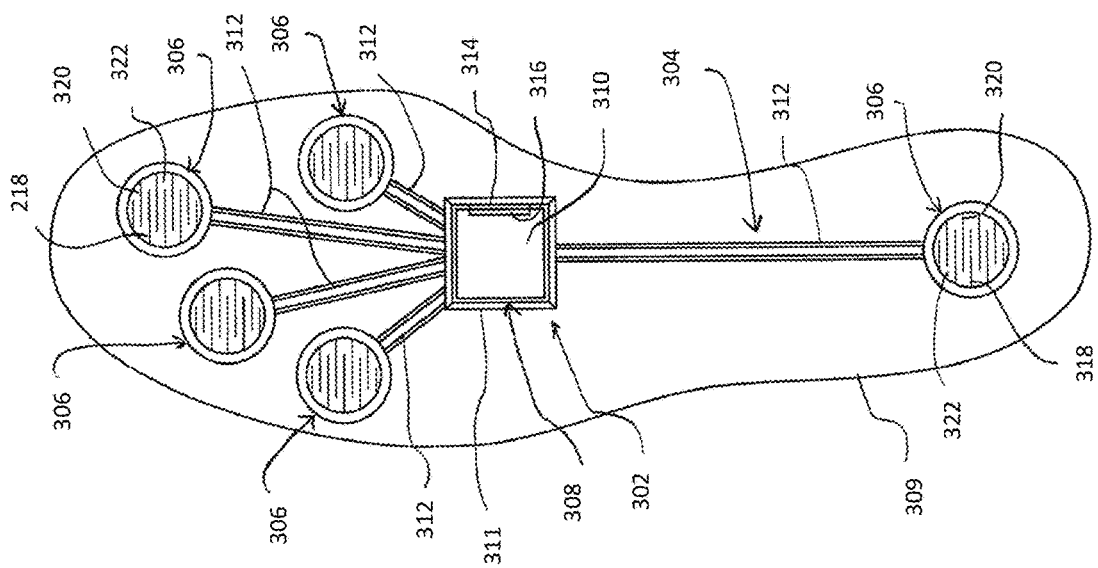
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
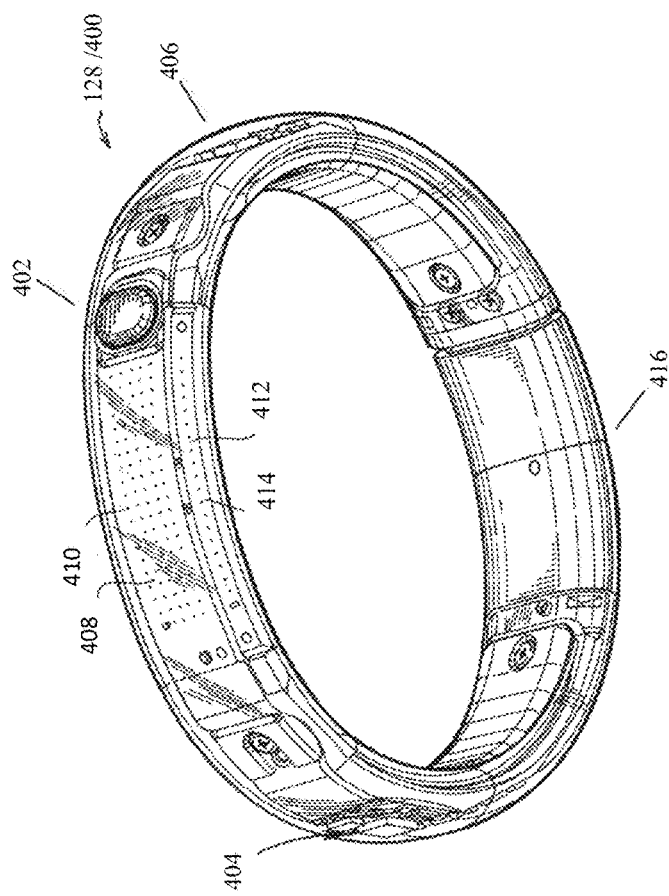
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
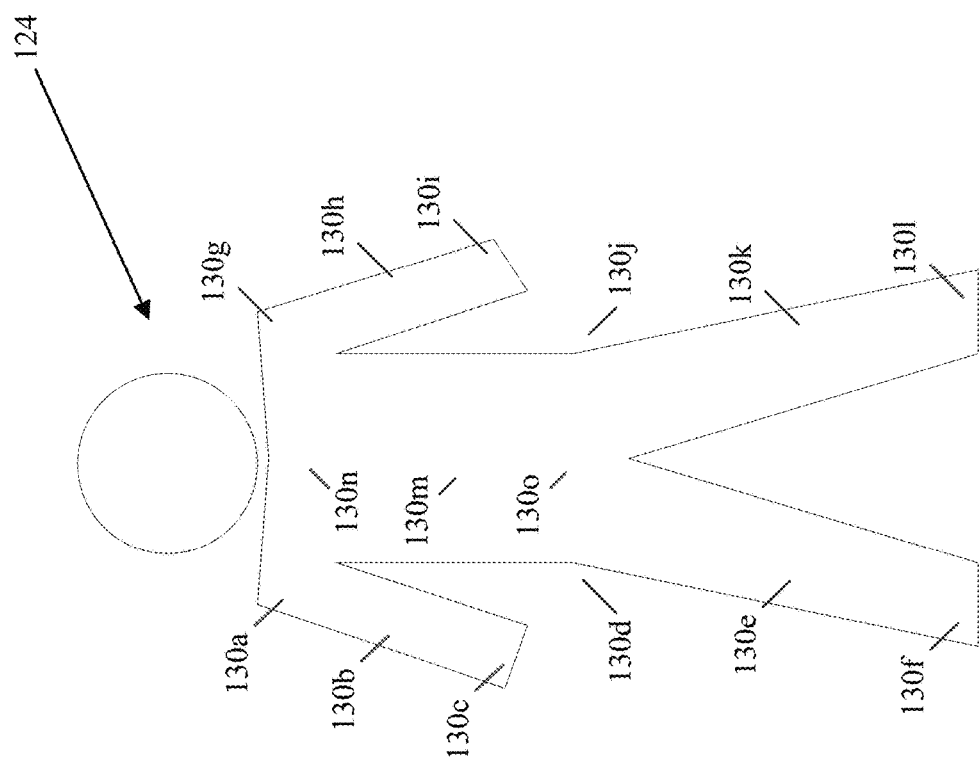
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306*n* may be located at about the sternum of user 124. Likewise, sensor location 130*o* may be located approximate to the naval of user 124. In certain embodiments, data from sensor locations 130*m*-130*o* may be utilized (alone or in combination with other data) to determine the center of gravity for user 124. In further embodiments, relationships between multiple sensor locations, such as sensors 130*m*-130*o*, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130*m*-130*o* may serve as a point for a center of moment location of user 124. In another embodiment, one or more locations may serve as a center of moment of specific body parts or regions.

Example Metrics Calculations

Aspects of this disclosure relate to systems and methods that may be utilized to calculate one or more activity metrics of an athlete, including but not limited to energy expenditure, speed, distance, pace, power, and/or others. The calculations may be performed in real time, such that the user may obtain real-time feedback during one or more activities. In certain embodiments, all calculations for a plurality of metrics may be estimated using a same set of attributes, or a sub-set of attributes from a common group of attributes, and the like. In one embodiment, a calculation of energy expenditure may be performed on a first set of attributes and without classifying the activity being performed by the athlete, such as being walking, running, playing a specific sport, or conducting a specific activity. In one embodiment, determinations of energy expenditure are done without any activity type templates, such that as the energy expenditure may be calculated from sensor data and/or derivatives thereof, without classifying the activity type. For example, energy expenditure may be calculated in accordance with certain embodiments using the same set of attributes regardless of whether the athlete is performing a first activity or a second activity, such as for example, walking or playing soccer.

In certain implementations, calculations of energy expenditure calculated may be performed using a first set of attributes and another metric, such as for example, speed may be determined from the same set of attributes or a subset of the same attributes. In one embodiment, determination of a plurality of metrics may be conducted using a selection of core attributes. In one example, this attribute calculation may be used to estimate energy expenditure and/or a speed of walking and/or running of the user. In one example, an energy expenditure and/or speed of walking and/or running may be estimated using a same set of attributes, or a sub-set of attributes from a common group of attributes, and the like.

The systems and methods described herein may compare calculated attributes from activity data (real-time activity data, and the like) to one or more models wherein the one or more models may not include data captured for the activity type that the athlete performed (and may not be categorized, such as for energy expenditure calculations). In this way, the one or more models may be agnostic to the specific activity being performed by a user. For example, an activity device may receive information from a user performing a basketball activity and at least one model may not contain any data from basketball activities.

As an example of calculating multiple metrics, systems and methods may be implemented to determine whether to calculate speed for one or more time windows of data. Certain aspects of this disclosure relate to determinations of speed or distance that comprises categorizing athletic data. As discussed above, however, other aspects relate to calculating energy expenditure values without categorizing the athletic data into activity types (walking, running, basketball, sprinting, soccer, football, etc.), however, categorizing at least a portion of the same data utilized to calculate energy expenditure for the calculation of other metrics, such as for example, speed and/or distance is within the scope of this disclosure. In one implementation, speed (or another metric) may be determined from at least a portion of data derived from the determination of energy expenditure values. In accordance with certain embodiments, the attributes are calculated on a single device, such as any device disclosed herein or known in the art. In one embodiment, the attributes and calculation of the metrics are calculated on a single device. In one such example, a device configured to be worn on an appendage of a user may be configured to receive sensor data and calculate the attributes and a plurality of metrics from the attributes. In one embodiment, the single device comprises at least one sensor configured capture data utilized to calculate at least one attribute. In accordance with certain embodiments, the attributes are calculated from one or more sensors located on the single device.

Example Energy Expenditure Calculations

One or more of the systems and methods described herein may calculate an estimate of energy expenditure. As such, one or more of the systems and methods described herein may implement at least one of the components of FIG. 6. Accordingly, in one example, FIG. 6 describes components that may be used to calculate energy expenditure from unprocessed sensor data, otherwise referred to as raw sensor data. In one configuration, a device, such as device 112, 126, 128, 130, and/or 400, may capture data associated with one or more activities being performed by a user. Said device may comprise one or more sensors, including, but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. This captured activity data may, in turn, be used to calculate one or more energy expenditure values associated with the user.

In one implementation, sensor data may be received from a first device, such as device 112, 126, 128, 130, and/or 400, wherein said first device may utilize a first operating protocol. This first operating protocol may include one or more processes configured to control the operation of/one or more tasks executed by, the first device. In one example, an operating protocol, such as the first operating protocol, may be referred to as an operating system, or program code, among others. Further, the first device may be associated with a first manufacturer, among others. In one example, data received from the first device may be received by a second device that utilizes a second operating protocol. Accordingly, said second device may include one or more of devices 112, 126, 128, 130, and/or 400, and such that the second operating protocol of said second device is not fully compatible with the first operating protocol. Those of ordinary skill in the art will recognize various incompatibilities that may arise with regard to different operating protocols. For example, data may be processed, manipulated, and/or formatted by the first operating protocol using a first syntax or methodology, and may be processed, manipulated, and/or formatted by the second operating protocol using a second syntax or methodology. In this way, the first operating protocol and the second operating protocol may generally be described as incompatible with one another, or not fully compatible with one another, among others. Accordingly, in one implementation, the systems and methods described herein may be utilized to calculate one or more energy expenditure values using data received from a first device that utilizes a first operating protocol, and received by a second device that utilizes a second operating protocol.

In one implementation, an estimation of the volume of oxygen consumed by a person may be used to calculate an effective metabolic equivalent, or an estimation of energy expenditure, by said person. For example, in one embodiment, a liter of oxygen consumed by a person may be associated with an energy expenditure of approximately 5 kilocalories (5 kcal). Additionally or alternatively, those of ordinary skill in the art will recognize that various alternative methodologies exist for calculation of energy expenditure based upon oxygen consumption by a person.

In one embodiment, oxygen consumption by a person may be measured as a volume of oxygen per unit mass, such as per kilogram ($VO_2$/kg). In one implementation, the systems and methods described herein may utilize values, such as stored as computer-executable instructions on one or more non-transitory computer-readable mediums related to actual and/or estimated oxygen consumption associated with specific activities. In certain embodiments, the values may be actual data or derived from actual data collected from one or more individuals performing one or more specific activities, and otherwise referred to as training data. For example, the systems and methods described herein may utilize training data related to oxygen consumption by one or more individuals performing activities including, among others, playing basketball, playing soccer, playing tennis, walking, jogging, running, and sprinting, sitting, squatting, and/or combinations thereof. Those of ordinary skill in the art will recognize various testing procedures that may be utilized to monitor oxygen consumption while an individual is performing one or more prescribed activities. Additionally, it will be readily understood to those of ordinary skill in the art that multiple oxygen consumption data points may be collected during an activity. Furthermore, one or more data manipulation processes may be performed on said collected data points to calculate, among others, an average oxygen consumption during a specific activity, and based on a recorded mass (e.g., measured in kilograms, and the like), and/or individual or class specific information (e.g., sex, weigh, height, age, percent body fat, among others).

In one implementation, training data may be recorded for one or more individuals performing one or more specific activities, wherein said training data includes information related to a volume of oxygen consumed at one or more time points during the one or more specific activities, and information related to individual and or class-specific information (e.g., the mass of the individuals performing the specific activities). Additionally, training data may include sensor data from a device, such as device 112, 126, 128, 130, and/or 400. In this way, the training day that may store information related to one or more sensor outputs in addition to information related to one or more volumes of oxygen consumed during one or more activities. In one implementation the sensor data stored in addition to the oxygen consumption data may include data from one or more of an accelerometer, a gyroscope, a location-determining device (e.g., GPS), light sensor, temperature sensor (including ambient temperature and/or body temperature), heart rate monitor, image-capturing sensor, moisture sensor and/or combinations thereof. For example, training data may include stored data from an accelerometer sensor, in addition to information related to a volume of oxygen consumed during an activity, for example, playing soccer.

Accordingly, the systems and methods described herein may include training data that includes one or more calculated attributes associated with an activity. Furthermore, the one or more attributes associated with an activity may include one or more volumes of oxygen consumed per unit mass of a person at one or more time points during an activity, and/or one or more calculated values based on one or more outputs from sensors associated with a device monitoring one or more motions of a user during said activity. For example, in one implementation, an output of an accelerometer sensor may include an acceleration value for each of the three axes (x-, y-, and z-axis). Accordingly, in one implementation, a plurality of acceleration values associated with the respective axes to which an accelerometer sensor is sensitive (x-, y-, and z-axis) may be grouped as a single acceleration data point. In another implementation, acceleration values may be processed by a processor, such as processor 202, associated with a device, such as device 112, 126, 128, 130, and/or 400 to calculate one or more attributes.

In one example, one or more data points received from a sensor aggregated into a dataset representative of one or more motions of user. Accordingly, the one or more data points may be processed to represent the data in a way that allows for one or more trends and/or metrics to be extracted from the data. In one example, acceleration data output from an accelerometer may be processed (transformed) to calculate a vector normal ("vector norm"). Additional or alternative transformations may be employed to calculate, in one example, a standard deviation of the vector normal, a derivative of the vector normal, and/or a Fast Fourier Transform (FFT) of the vector normal. Those skilled in the art will appreciate that certain transformations may combine sensor data from two or more sensors and/or with other data, such as biographical data (e.g., height, age, weight, etc.). In other embodiments, transformation may only utilize data from single sensors, such that sensor data from multiple sensors is not mixed.

In one example, one or more attributes may be calculated from the received data, and wherein the attributes may be calculated subsequent to one or more transformation processes be executed on a dataset representative of one or more motions of a user. In this regard, datasets from multiple users may be used as a comparison against a user whose activity is not within the dataset. This may be done without categorizing the user's activity into an activity type (e.g., walking, running, playing specific sport) and in certain embodiments, the user may be performing an activity that was not conducted as part of collecting the training data within the data used to obtain attribute values for the models.

In another example, the systems and methods described herein may be implemented to estimate one or more metrics from sensor data. These metrics may include, among others, an estimation of energy expenditure, an estimation as to whether a user is running, walking, or performing other activity, and/or an estimation of a speed and a distance (a pace) which a user is moving, and the like. For example, block 601 of flowchart 600 from FIG. 6 shows an example implementation of calculating energy expenditure from one or more attributes. Separately, block 603 is directed to an example implementation for calculating speed, which may be determined using one or more calculated attributes, which may be derived from the same sensors, from the same data, and/or the same attributes as the energy expenditure metric.

Accordingly, the systems and methods described herein may utilize data received from one or more different sensor types, including, among others, an accelerometer, a heart rate sensor, a gyroscope, a location-determining device (e.g., GPS), light (including non-visible light) sensor, temperature sensor (including ambient temperature and/or body temperature), sleep pattern sensors, image-capturing sensor, moisture sensor, force sensor, compass, angular rate sensor, and/or combinations thereof. Furthermore, one or more components of flowchart 600 from FIG. 6 may be implemented by a first device that utilizes a first operating protocol, and using data received from a second device that utilizes a second operating protocol, and the like.

Furthermore, while the example of attributes associated with acceleration data output from an accelerometer sensor are described, those of ordinary skill will appreciate that other sensors may be used, alone or in combination with other sensors and devices, without departing from the scope of this disclosure. For example, a heart rate monitor may be used, wherein the data output from a heart rate monitor may output data representative of a heart rate in units of beats per minute (BPM) or equivalent. Accordingly, one or more transformations may be performed on outputted heart rate data to interpolate a heart rate signal between heart rate data points, and allowing for signal dropouts at certain points. Furthermore, the attributes calculated for sensor data associated with a heart rate monitor, or any other sensor, may be the same, or may be different to those described above in relation to accelerometer data.

In another implementation, the systems and methods described herein may analyze sensor data from combinations of sensors. For example, a device may receive information related to a heart rate of a user from a heart rate monitor, in addition to information related to motion of one or more appendages of a user (from one or more accelerometers, and the like). In one example, the device may determine that a user has a heart rate indicative of vigorous exercise, but accelerometer data may indicate that said user has been at rest for a period of time. Accordingly the device may determine that the user has a sustained elevated heart rate after a period of activity but is now resting after said activity, and the like.

In one implementation, training data may be used to construct one or more models, otherwise referred to as experts, or expert models, for predicting, among others, a volume of oxygen consumption based upon (at least in part) one or more individual-specific properties such as a gender, a mass and/or a height of a user. Accordingly, information from one or more sensors associated with a device, such as device 112, 126, 128, 130, and/or 400, may be used to calculate one or more attributes. In turn, the calculated attributes may be compared to attributes associated with one or more constructed models, and thereby, used to predict a volume of oxygen being consumed by a user while outputting motion signals (sensor output values) corresponding to the calculated attributes. For example, a user may be performing an activity, such as playing soccer, while wearing a sensor device on an appendage. The sensor device, in turn, may output sensor values, which may be processed to calculate one or more attributes. Subsequently, the one or more calculated attributes may be compared to one or more attributes associated with one or more models, and an estimation of a volume of oxygen being consumed by the user while playing soccer may be made. Furthermore, said estimation of a volume of oxygen being consumed may be used to estimate energy expenditure values by the user playing soccer. This process is described in further detail in relation to FIG. 6. In certain embodiments, all of the sensor data comes from a unitary device. In one example, the unitary device is an appendage-worn device. In certain configurations, the appendage worn device comprises at least one of an accelerometer, a location-determining sensor (e.g., GPS) and a heart rate monitor. In another example, the unitary device comprises a sensor configured to be placed on or within athletic apparel, such as a shoe. In yet another example, a sensor from at least two different devices are utilized to collect the data. In at least one embodiment, the device comprising a sensor utilized to capture data is also configured to provide an output of energy expenditure. In one embodiment, the device comprises a display device configured to display an output relating to energy expenditure. In further embodiments, the device may comprise a communication element configured to transmit information relating to energy expenditure to a remote device.

In another implementation, one or more attributes may be calculated from received sensor data and used as inputs to one or more walking and/or running models for predicting, among others, a speed/a pace of a user. Further details of such an implementation are described in relation to block 603 of flowchart 600.

FIG. 6 is a flowchart showing an exemplary implementation of attribute calculation. In one example, this attribute calculation may be used to estimate one or more metrics associated with an activity being performed by a user, and wherein said estimation may include an energy expenditure speed, and/or one or more other metrics. In one example, an energy expenditure and/or speed of walking and/or running may be estimated using a same set of attributes, or a sub-set of attributes from a common group of attributes, and the like.

Information related to the movement of the user may be outputted as one or more data signals from one or more sensors associated with one or more sensor devices monitoring the user. In one implementation, FIG. 6 represents one or more processes carried out by at least one processor, such as processor unit 202, which may be associated with a sensor device, such as, among others, device 112, 126, 128, 130, and/or 400. Accordingly, devices may not directly monitor a volume of oxygen being consumed by a user during an activity. In one implementation, one or more sensor devices may monitor one or more motions associated with one or more activities being performed by a user. Furthermore, in one arrangement, received activity data may be correlated with observed oxygen consumption values for activities that may exhibit certain attributes, and associated with one or more oxygen consumption models.

One or more embodiments receive sensor data from one or more sensors (see, e.g., block 602). In certain embodiments, the sensor data may be associated with a device worn by a user. In one example, and as previously described, said device may be, among others, device 112, 126, 128, 130, and/or 400. Accordingly, the sensor data may be received by a processor, such as processor 202 from FIG. 2, and may be received from one or more sensors described herein and/or known in the art. In one implementation, sensor data may be received at block 602 from an accelerometer at a frequency of, among others, 25 Hz. Additionally or alternatively, sensor data may be received from the sensor, such as accelerometer, in windows of between 5.0 and 5.5 seconds. In one embodiment, the window (or time frame) may be about 5.12 seconds in length. A window may be a period of time during which sensor data is recorded for one or more motions of a user associated with one or more activities being performed by a user. In one implementation, a sample window may include 128 samples (data points) of sensor data, wherein a sample of sensor data may include a value for each of three orthogonal axes of an accelerometer (x-axis, y-axis, and z-axis), and/or a vector normal value. In yet another implementation, sensor data received from, in one implementation, an accelerometer, may be received in windows that do not overlap (e.g., 5.12 second-length groups of sensor data each containing 128 samples, and received singly, rather than simultaneously, and/or discrete from each other). However, in alternative embodiments, those of ordinary skill will readily understand that the systems and methods described herein may be employed with any frequency of operation of an accelerometer, with a window length measuring any length of time, and using any number of samples of sensor data from within a given window. Data may be validated as it is received, such as for, for example, at block 604. Data validation may include, among others, a person of one or more values of received sensor data to one or more threshold values, and the like.

Further aspects of this disclosure relate to calculating one or more attributes from the data (see, e.g., block 606). Calculation of one or more attributes may occur after validation protocols, such as those described herein. In one implementation, one or more attributes may be calculated for one or more of the received samples in a sample window (e.g., the 128 sample window described above). Attribute calculation may occur in real-time as the data is collected Further embodiments may compare one or more calculated attributes associated with data received from one or more sensors, and indicative of one or more activities being performed by a user, to one or more attributes associated with one or more models. In one example, one or more attributes may be compared to one or more models (see e.g., block 608). For example, for calculations of energy expenditure, one or more attributes may be compared to oxygen consumption models. In another example, attributes may be used as inputs to one or more of, among others, models for estimation of a number of steps (during walking), strides (during running), or other movements by a user, and/or models for estimation of speed and distance (pace) of a user (see e.g., block 603 of flowchart 600). Furthermore, as will be apparent from FIG. 6, one or more calculated attributes may be used as inputs to one or more models such that, in one example, a model for estimation of an energy expenditure may be executed separately from a model for calculation of a step rate, a walking speed, and/or a running speed, and the like. As previously described, one or more models may be stored in a memory, such as memory 212, and the like, and associated with a device, including a sensor device.

In one implementation, a model may include information (e.g. training data) collected during one or more user's performance conducting one or more activities and, in one example, predicted oxygen consumption. The models may include training data from activities that, despite being different from the activity that an athlete is performing, may have similar relationships between attributes. As such, the models may serve as accurate predictors of oxygen consumption. Accordingly, a model may include training data associated with one or more different activities. For example, a model may include training data received from one or monitoring processes associated with, among others, playing soccer and playing basketball. In this way, oxygen consumption data associated with certain movements of soccer and basketball activity data may be similar (within one or more predetermined numerical ranges for different periods during the activities, and the like).

In another implementation, a first oxygen consumption model may comprise data from a same one or more users as those one or more users' data used in a second oxygen consumption model. In another configuration, a first model and a second model may use a same one or more users' data. In yet another configuration, a data associated with a model may have been captured from a same one or more users during a single data collection period, or from multiple collection periods across a same or a different day, and the like. In one implementation, a first model may be associated with data from a first group of one or more sensors and a second model may be associated with a second group of one or more sensors, and wherein the first group may share one or more, or none of the same sensor types. In one implementation, the systems and methods described herein may compare calculated attributes from activity data (real-time activity data, and the like) to one or more models wherein the one or more models may not include data captured for that activity type. In this way the one or more models may be agnostic to the specific activity being performed by a user. For example, an activity device may receive information from a user performing a basketball activity. In response, the device may process the received basketball activity data (such as, for example, block 606 of flowchart 600), and compare calculated attributes to one or more models (such as, for example, block 608). In one implementation, the one or more models may or may not comprise data related to basketball. In this way, the computed one or more attributes for received sensor data may correspond to one or more models, and wherein the models need not comprise training data related to the specific activity being performed by a user.

In one configuration, a plurality of models, each with their own attributes, which may or may not overlap attributes of other models, may be utilized. In one example implementation, each model may be associated with 20 attributes. In another configuration, the systems and methods described herein may store 5, 10, 15 or 21 attributes for each model. However it will be readily understood to those of ordinary skill that the systems and methods described herein may store any number of attributes in association with each model, and in certain embodiments a first number of attributes stored in association with a first model may differ from a second number of attributes stored in association with a second model. Furthermore, the one or more attributes stored in association with a model may be alternatively referred to as weights, or may be used to calculate related weighting values that may be used to compare a model to those attributes calculated from sensor data received from a device. Accordingly, in one implementation, the number of attributes calculated from data received from a sensor device (or multiple sensor devices) collecting movement data of a user may be equal to a number of attributes, or alternatively, a number of weights associated with one or more stored oxygen consumption models.

One or more aspects may calculate a probability that a first model will provide the most accurate estimation of oxygen consumption from the total number of stored one or more models. For example, a probability that a specific model, from a group of different (e.g., 16) models is most likely to provide the most accurate output of oxygen consumption may be calculated. The calculations may be performed, for example, as part of block 608, and be based on one or more attributes calculated from received sensor data indicative of an activity being performed by a user. In one implementation, a level of closeness between attributes calculated from received sensor data, and those attributes, or alternatively, those weights, associated with one or more of the stored oxygen consumption models may be calculated, such as for example as part of block 608. In one implementation, the systems and methods described herein may execute one or more processes to compare input attributes with corresponding weights associated with a stored model (expert). In one example, block 608 may calculate a probability for each stored model. Accordingly, said probability may represent a likelihood that the calculated one or more attributes are a best-fit for a given model. For example, a probability may be calculated for each of 16 stored models, and the like. The highest probability value, from the 16 calculated probabilities, indicates the model with the best-fit for the calculated attributes, and the like.

In one example, block 610 represents one or more processes to select a model with a best-match, or best-fit to those calculated attributes from block 608. As previously described, said best-fit model represents stored training data that most closely approximates the data received from a sensor device monitoring an activity of the user. In one implementation, the best-fit model may be the model corresponding to a calculated probability value that is closest to a value of 1.0. In another implementation, block 610 may select two or more models. For example, models fitting within a predefined deviation, variation, and/or threshold may be selected (referred to as a hybrid-model strategy).

As shown by illustrative block 612, one or more embodiments may estimate an output value from a selected model (expert). In one example, an output may be in estimation of a volume of oxygen consumption as a result of one or more activities being performed by a user. Accordingly, in one example, block 612 may correlate an activity being performed by a user with an estimated oxygen consumption value, and based on a selected model (e.g., a best-fit model) that most closely matches attribute values calculated from sensor data. In one implementation, a model may store one or more estimates of oxygen consumption, wherein the one or more estimates of oxygen consumption may be stored based on at least one individual-specific value, such as a gender, a weight and/or a height of a user. Accordingly, and based upon the one or more attributes associated with the sensor data received from a sensor device, block 612 may return an estimate of a volume of oxygen consumption by the user based upon an activity carried out by the user.

Block 614 may be implemented to estimate a motion metric associated with a model output value. In one example, a motion metric may be an energy expenditure value, which may be estimated using an oxygen consumption value. As previously described, one or more methods may be utilized to calculate an energy expenditure from an oxygen consumption value. In one example, an estimated energy expenditure of 5 kcal is associated with an oxygen consumption of 1 L by a user. However those of ordinary skill in the art will recognize various other formulae for calculating energy expenditure based upon a value of oxygen consumption, and using one or more individual-specific values (e.g., a height and a weight of a user).

In another implementation, one or more attributes calculated (including, e.g., at block 606) may be used in a determination of whether sensor data is indicative of walking, running, or another activity being performed by a user, and additionally or alternatively, the speed at which the user is walking or running, and the like. Accordingly, one or more attributes calculated at block 606 may be used as inputs to block 603. In particular, one or more attributes may be communicated from block 606 to decision block 616. At block 616, one or more processes may be executed to determine whether a user is running or walking, or performing another activity. If it is determined that a user is performing an activity other than running or walking, flowchart proceeds from block 616 to 618. Accordingly, for a user performing activity other than running or walking, no processes are executed to define the speed at which the user is traveling, and the like. If it is determined, at decision 616, that's the user is running or walking, decision 620 may be implemented to determine whether the activity is walking or running. Example embodiments for selecting an activity, such as running or walking, are provided herein, including in relation to In one embodiment, if it is determined that a user is running, one or more attributes may be communicated to a running model, such as to determine speed (e.g., see block 622). If, however, it is determined that a user is walking, certain embodiments may communicate one or more attributes to a walking model, such as to determined speed (e.g., block 624).

In another implementation, the systems and methods described herein may be utilized to calculate energy expenditure using one or more metrics received from an activity device, such as device 112, 126, 128, 130, and/or 400. As such, the one or more metrics may include activity metrics related to an activity being performed by a user. Examples of activity metrics may include, but are not limited to, speed, pace, acceleration, volume of oxygen consumption, a metabolic equivalent value, a calorie consumption value, a power, a heart rate, a gradient, or a temperature, among others. Accordingly, in one example, flowchart 700, schematically depicted in FIG. 7A, may describe one or more processes for calculation of an energy expenditure value of a user from data received from an external device. Further, in one implementation, one or more components of flowchart 700 may be executed by one or more devices utilizing a first operating protocol, and using data received from one or more separate devices utilizing a second operating protocol. As such, these first and second operating protocols may have incompatibility issues, as previously described in this disclosure.

Figure 7A:
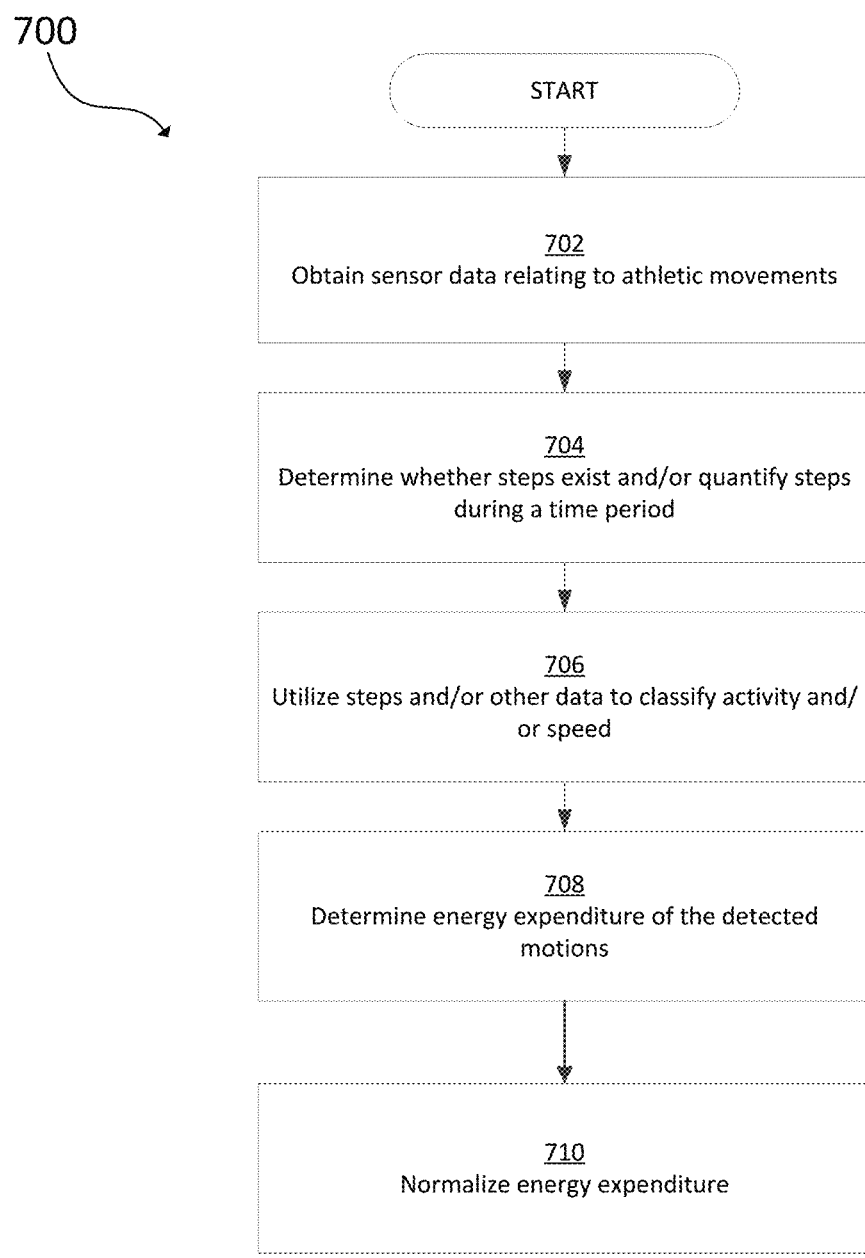
FIGS. 7A and 7B show example flowcharts that may be utilized to classify activity and/or calculate energy expenditure values of an individual.

In one specific example, one or more components of flowchart 700 and FIG. 7A may be executed by a device, such as device 112, 126, 128, 130, and/or 400, as previously described. In one embodiment, sensors solely located on a device configured to be worn by a user, such as a wrist-worn device, may be utilized to detected motion parameters. Data from sensors on such as device may be used without the assistance of other sensors in one or more determinations relating to classifying activity and/or determine energy expenditure. The activity may include athletic and/or other physical activity of user 124. In one implementation, FIG. 7A schematically depicts flowchart 700 having an illustrative process that may be utilized to classify activity and/or calculate energy expenditure values of an individual in accordance with one embodiment. FIG. 7A is provided as an overview of exemplary embodiments that may comprise a plurality of sub-elements. In this regard, the remaining figures (and related disclosure) following FIG. 7A may optionally be used in conjunction with FIG. 7A and/or each other to provide a full system that obtains sensor data and provides energy expenditure values. In accordance with other embodiments, one or more different systems and methods discussed below may be used alone or in combination with only a portion of other disclosed systems and methods to provide one or more of: step counts, activity classifications, and energy expenditures, among others. Various embodiments of step quantification systems and methods may relate to a low power, high fidelity, integer-based step counter using a multi-tier technique. These and other embodiments are described below.

In accordance with a first embodiment, a plurality of samples from one or more sensors associated with one or more devices (e.g., devices 112, 126, 128, 130, and/or 400) may be obtained during a first time period (see, e.g., block 702). In certain configurations, at least one sensor (e.g. sensor 128) may comprise an accelerometer. The accelerometer may be a multi-axis accelerometer. In another embodiment, however, a plurality of accelerometers may be utilized. Other non-accelerometer based sensors are also within the scope of this disclosure, either in combination with an accelerometer or individually. Indeed, any sensor(s) configurable to detect or measure athletic movement and/or physiologic properties are within the scope of this disclosure. In this regard, data may be obtained and/or derived from a plurality of sensors, including for example, location sensors (e.g., GPS), heart rate sensors, force sensors, gyroscope, etc. In one embodiment, various systems and methods are implemented, at least partially, on a portable device. In certain embodiments, the portable device may be a wrist-worn device (see, e.g., sensor 128). In one embodiment, sensor data from a device configured to be worn on a human appendage (e.g., wrist, arm, neck, ankles, leg, etc.) may be utilized without other sensor data. Motion data, such as measured through an accelerometer and/or other sensors, may be loaded into a multi-segment threshold based acceleration buffer.

Further aspects relate to detecting and/or measuring an athletic parameter, such as for example, a quantity of steps taken by a user, such as user 124. One or more system or methods may utilize various portions of the data (such as in an acceleration buffer comprising accelerometer data) to determine if detected parameters are indicative of a specific action or activity. In one embodiment, a quantity of steps may be detected during a predefined period of time (See, e.g., block 704). Various different systems and methods may be utilized to quantify a number of steps taken by the user during a time period (or even determine whether steps exist in the sensor data). In one implementation, systems and methods for quantifying steps taken by user over a given time period are described in FIGS. 4-8 of U.S. application Ser. No. 13/744,103, filed 17 Jan. 2013, the entire contents of which are incorporated herein by reference for any and all non-limiting purposes. In one example, step data and/or other motion data may be utilized in the classification of activity, such as either walking or running, for example (see, e.g., block 706). In certain implementations, if data cannot be categorized as being within a first category (e.g., walking) or group of categories (e.g., walking and running), a first method may analyze collected data. In one example, if detected parameters cannot be classified, then a Euclidean norm equation may be utilized for further analysis. In one example, an average magnitude vector norm (square root of the sum of the squares) of obtained values may be utilized. In yet another example, a different method may analyze at least a portion of the data following classification within a first category or groups of categories. In one example, a step algorithm, such as those disclosed herein, may be utilized.

Further examples may utilize the classified activity data and/or unclassified activity data to estimate the energy expenditure of the user's detected motions as sensed by one or more of the sensors (e.g., block 708).

Further examples relate to adjusting energy expenditure values according to at least one activity factor. In some examples there is not a one-to-one correlation between an activity and an activity factor. The selection of an activity factor may be based on several different variables, such as the activity identified, steps taken, heart rate, and intensity of a workout.

Aspects of various examples may offer one or more advantages and/or benefits over the prior-known systems and methods. In certain implementations, false positives are reduced or eliminated for short-duration arm movements using a buffer filling strategy. Using a constrained search for analysis (e.g. FFT) may assist in selecting the correct frequency (e.g., frequencies relating a vertical bounce rather than the arm swing such that the correct walking frequency is obtained for two feet steps). In further examples, the overlapping of motion data windows may allow for improved detection of short bursts of activities (e.g., step activities). Finally, the frequency analysis may be performed on one combined channel of sensors so that arm rotation does not throw off detection and measurement of sensor outputs. Furthermore, by combining accelerometer channels, less analysis (e.g. Fourier transform frequency analyses) may be performed. This may improve battery life. One or more of these advantages may be realized on a portable device configured to be worn on an appendage of the user during the performance of the physical motions.

In one implementation, process 700 may normalize a calculated energy expenditure value. As such, in one example, process 700 may execute one or more normalization processes at block 710.

Accordingly, one or more normalizing/normalization processes, such as those executed at block 710, may be used to calculate an athletic metric, such as a cumulative energy expenditure value, which may be expressed as, for example, caloric expenditure. Based on one or more criterion, such as the classification of the user activity, one or more normalizing factors (or processes utilizing one or more factors) may be determined. For example, in one embodiment, at least one of user's 124 activity may be classified (e.g., such as at block 710 of flowchart 700 shown in FIG. 7A, or block 734 of flowchart 720 shown in FIG. 7B) and one or more corresponding normalizing factors applied to the athletic metric. In one example, application of normalizing factors to activity classification (or other variable(s)) to create a normalized athletic metric may allow for an improved comparison of activity levels of athletes and/or may promote collaboration among users, normalize results for competition among users of different capabilities, and otherwise encourage activity. In one embodiment, a normalized energy expenditure value may be calculated as follows:

$$NEEVs = AF * duration \qquad \text{(equation 1)}$$

Wherein:
NEVs=Normalized Energy Expenditure Values
AF=activity factor
duration=duration of the activity classified in step 706

Block 706 may be performed at a device that includes sensors that monitor activity and/or at another device that includes a processor, such as a mobile phone (see, e.g., 112) or server (see, e.g., 111).

In some embodiments equation 1 may be modified to include a scalar that is multiplied by the activity factor and duration. The scalar may be selected so that typical energy normalized expenditure points fall within a desired range. The range of values may be desired for various games or competitions.

Variations of equation 1 may be used in other embodiments of the invention. For example, NEEVs (or other metrics) may be calculated with formulas that utilize a MET value, a RMR value, a duration and/or a scalar. In one embodiment, NEEVs calculated as follows:

$$NEEVs = MET\ value * duration * RMR * scalar \quad \text{(equation 2)}$$

Wherein:

MET value=metabolic equivalence value, which may be determined in block 704 duration=duration of an activity, such as an activity classified in block 706

RMR=resting metabolic rate

Scalar=a number, which may be uniformly applied or variable based upon one or more factors.

The RMR used may be a calculated RMR or a default RMR. A calculated RMR may be a function of factors such as a user's height, age, weight, gender and/or other demographic or physiological parameters. In certain embodiments, one or more factors may be obtained and/or derived from one or more sensors associated with one or more of devices 112, 126, 128, 130, and/or 400, and thus may not have to be specifically defined by user 124 or source of data associated with the received athletic metric. A default RMR may be a value believed to correspond a relatively large number of users. In alternative embodiments a default RMR may correspond to an RMR of a well-known athlete, celebrity or a famous person. The use of a default RMR may allow the comparison of activity levels among many different users that otherwise could not or would not be compared. A default RMR may also promote collaboration among users, normalize for competition among users of different capabilities, and/or otherwise encourage activity.

As shown in equation 2, a scalar may be optionally implemented. The scalar used in equation 2 may, but is not required to be, a whole number, such as 1, 3, 5 or 10. In some embodiments, the scalar is selected so that typical energy expenditure points fall within a desired range. The range of points may be desired for various games or competitions, and/or to provide a relation to a virtual currency or point system. Different and varying equations may be selected for different games, activities, population dynamics, and competitions. In one example a group may set handicaps among the players based on fitness, so that NEEVs may only be generated for those athletes that do a common activity or set of activities for longer period(s) of time. A group of users participating in an energy expenditure point competition may agree on a particular equation or method before beginning the competition. Yet, in other embodiments, NEEV calculation may not be explicitly disclosed to one or more athletes or users so as to prevent or attempt to prevent athletes from attempting to maximize points or otherwise "earn" values from conducting activities that exploit one or more imprecisions in the system. As those skilled in the art will appreciate, every model will have limitations. And in this regard, aspects of this innovation attempt to minimize inaccurate and/or imprecise data values via one or more systems and methods disclosed herein. In some embodiments of the invention, a user may participate in multiple competitions and earn different values for the same activity because of different calculation methods. For example, a user may be participating in two competitions that have unique calculation methods. The user may earn two different point totals for the two different games and a third point total for their overall energy expenditure. Some point totals may be maintained separate from an overall point total.

In those embodiments in which the athletic metric relates to energy expenditure in which METs are utilized, some activities, games and/or competitions may limit awarding energy expenditure points for activities that have relatively low MET values. In some embodiments, awarding energy expenditure points for activities that have relatively low MET values may also be limited all of the time or in other situations. An optional step may be added to the process shown in FIG. 7A or other implementations to not award points for activities that do not exceed a MET threshold value. For example, an exemplary threshold value may be 1.0, 2.0 or 3.0. In another embodiment, the threshold value may equal 2.8. Different games and competitions may use other threshold values. When the MET value does not exceed the threshold, a step may be implemented to disregard the corresponding activity and not use the activity when calculating energy expenditure points.

Another embodiment could have the threshold generally applied, but not when games or competitions are underway, or at least certain games or competitions. The games or competitions may be based on all values. In another embodiment, a threshold may always apply even to games and competitions. In another embodiment, different thresholds may apply by activity, game and/or competition, e.g., one for running briskly, one for running, one for walking, and a default.

In certain implementations, such as after at least one of user's 124 activity is classified according to one embodiment, block 704 may be implemented to determine a corresponding MET value. For example, the MET value may correspond to brisk running, running at a moderate pace, walking slowly or any other activity found in conventional MET tables. If an activity was not classified, such as in block 704, a default MET value may be selected or derived. In some embodiment multiple default MET values may be utilized. An activity's intensity, duration or other characteristic(s) may be assessed, from which one or more default METs may be applied. These plural METs may be set via medians/averages, ranges, or other statistical approaches.

Alternative embodiments may use alternative or additional equations for calculating point values and/or other quantities. The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity values or normalized energy expenditure values and/or steps. Calculating values that are functions of activity values or NEEVs and other variables may be used to compare the efficiencies of various activities. For example, an equation may be used to determine that taking steps at a faster pace may result in activity values or NEEVS accumulating at a faster per step pace. Another exemplary equation may determine activity values or NEEVs per a predetermined distance or a unit of distance.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity values or NEEVs may be displayed to a user via display 235 or a display that is part of a mobile device.

Either before, during and/or after the normalized values are calculated, the calculated values (raw, processed, or NEEVs) may be combined, such as being added, to a total in step 708. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the values earned for each activity may be a function of a corresponding activity factor.

Figure 7B:
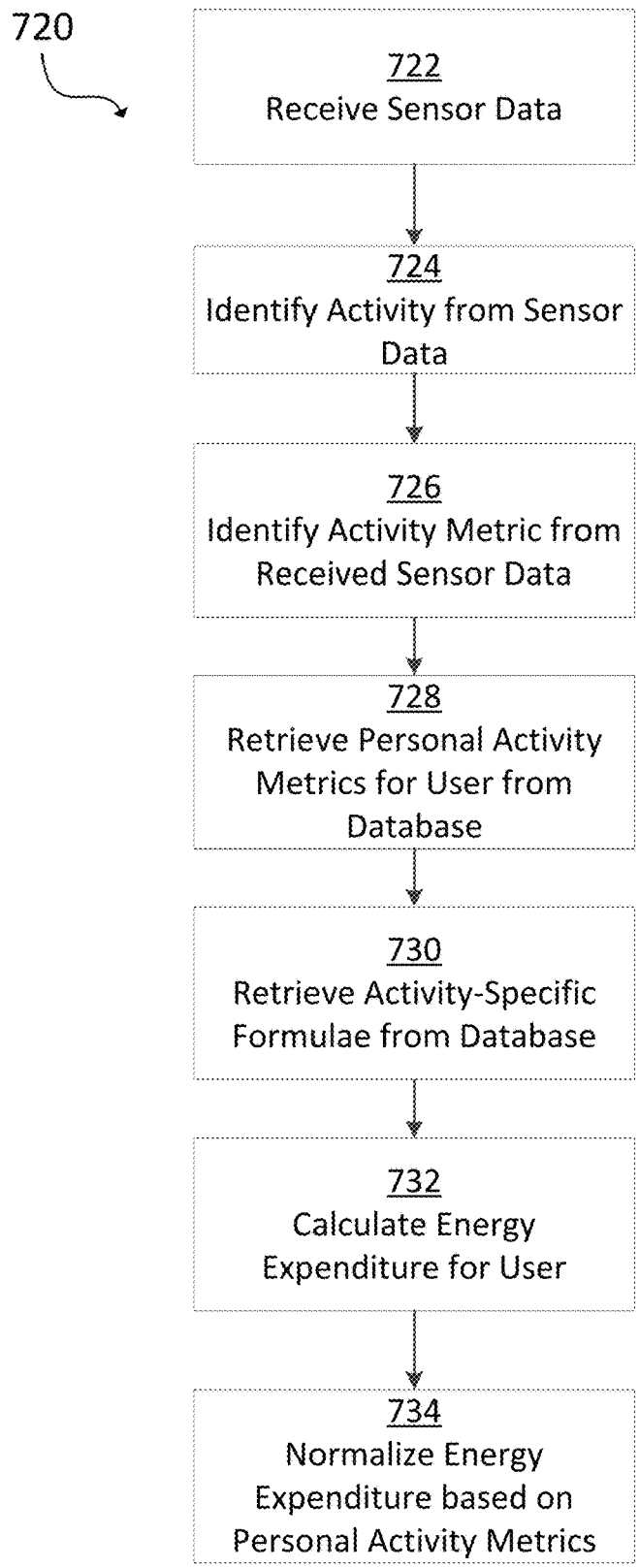

Various additional or alternative methodologies for calculation of energy expenditure of a user from received activity metrics may be utilized, without departing from the scope of the disclosures described herein. FIG. 7B schematically depicts one implementation of flowchart 720 that may be executed to calculate energy expenditure of a user. Accordingly, in one example, flowchart 720, similar to flowchart 700, may be executed by a first device, such as device 112, 126, 128, 130, and/or 400, and utilizing data received from a second device, such as device 112, 126, 128, 130, and/or 400. Further, the first device and the second device may be associated with different operating protocols, or manufacturers, among others.

In one example, flowchart 720 may receive data from one or more sensor devices. Those of ordinary skill in the art will recognize that these one or more sensor devices may be worn by a user, or may generate sensor data using remote sensing of user movement (e.g. remote imaging technologies configured to track user movement, and the like). As such, flowchart 720 may receive sensor data communicating information related to an activity being performed by a user. The sensor may comprise one or more of an accelerometer, a GPS sensor, a heart rate sensor, a barometric pressure sensor, a thermometer, an ambient light sensor, or a compass sensor, among others. In one example, the sensor may be included in one or more of devices 112, 126, 128, 130, and/or 400, as previously described in this disclosure. Accordingly, in one implementation, sensor data may be received at block 722 of flowchart 720.

In one implementation, received sensor data may include information identifying an activity being performed by a user. As such, received sensor data may include information identifying a sport, or another physical activity, that a user is currently participating in, or previously participated in. In one example, one or more activity recognition processes may be executed by a sensor device in order to identify one or more activities being participated in by a user. Those of ordinary skill in the art will recognize various activity recognition processes that may be executed in this regard. As such, in one example, an activity may be identified from received sensor data at block 724. In this way, in one implementation, one or more activity recognition processes may be executed separately to flowchart 720 by a separate device. However, those of ordinary skill in the art will recognize that one or more activity recognition processes may be executed at block 724 to identify an activity associated with received sensor data, without said activity being explicitly identified in received sensor data. As such, in one example, a receiving device may identify one or more sensor data patterns from received sensor data in order to identify one or more activities being participated in by a user.

In one example, one or more activity metrics may be identified from received sensor data. These activity metrics may include values utilized to quantify one or more physical movements of a user. As such, an activity metric may include, among others, a speed, a pace, an incline on which a user is moving, a heart rate, a metabolic equivalent value, a calorie consumption value, a volume of oxygen consumption, or a power value. In this way, flowchart 720 may receive one or more activity metrics calculated by one or more separate devices, such as one or more of devices 112, 126, 128, 130, and/or 400. In one example, flowchart 720 may identify these one or more activity metrics at block 726.

In one implementation, in order to calculate an energy expenditure for a user, one or more personal activity metrics may be retrieved from a database. For example, an energy expenditure of a user may be based upon one or more of a user height, weight, a gender, a resting heart rate value, and/or a metric recording a baseline level of physical fitness, among others. As such, these one or more personal activity metrics may be stored in a database, such as in one or more of devices 112, 126, 128, 130, and/or 400, or server 111. Accordingly, those of ordinary skill in the art will recognize various network communication topologies and/or protocols that may be utilized to access database information stored remotely or locally, or combination of both, and without departing from the scope of the disclosures described herein. In one example, flowchart 720 may retrieve one or more personal activity metrics from a database at block 728.

In one implementation, in order to calculate an energy expenditure value of the user, flowchart 720 may utilize one or more activity-specific formulae. For example, an energy expenditure value may be calculated based upon an activity identified at block 724, and using one or more formulae specific to the identified activity. As such, in one example, flowchart 720 may retrieve activity-specific formulae from a database, such as from one or more of server 111 and/or devices 112, 126, 128, 130, and/or 400. In one example, the activity-specific formulae may be retrieved from a same database as the personal activity metrics from block 728. In one implementation, the retrieval of these activity-specific formulae may be executed at block 730.

In one example, flowchart 720 may execute one or more processes to calculate an energy expenditure of the user using the received sensor data in combination with the one or more retrieved personal activity metrics and activity-specific formulae. As such, in one example, a calculated energy expenditure for a user may output a numerical value corresponding to energy used by a user over a given time period while participating in one or more physical activities. In one example, a calculated energy expenditure may be expressed in units of joules or calories, among others. Accordingly, the calculation of energy expenditure value for user may be executed at block 732 of flowchart 720.

In one implementation, one or more processes may be executed to normalize a calculated energy expenditure value for a user. As such, this normalization may allow for comparison of a calculated energy expenditure value to corresponding energy expenditure values calculated for one or more other individuals, and such that factors of gender, height, weight, and/or a baseline level of physical fitness are taken into account. Accordingly, this normalization may be executed at block 734 of flowchart 720, and may be similar to one or more processes executed at block 710 of flowchart 700.

Figure 8A:
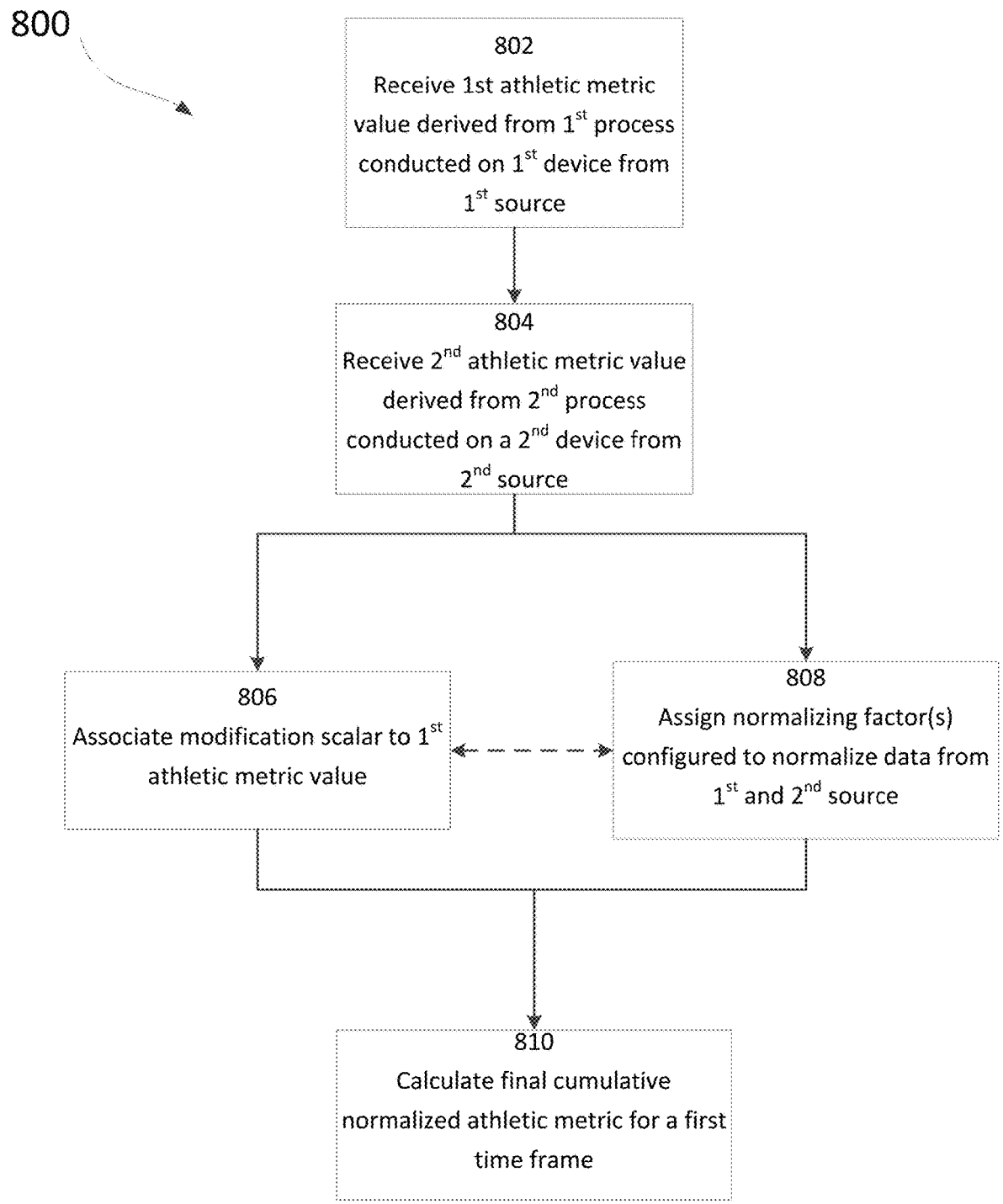
FIG. 8A illustrates an example flow diagram which may be used in calculating a cumulative energy expenditure estimate based on energy expenditure estimates obtained by two or more different processes, which may conducted on entirely different devices incapable of communicating with each other, either directly or indirectly.
Figure 13:
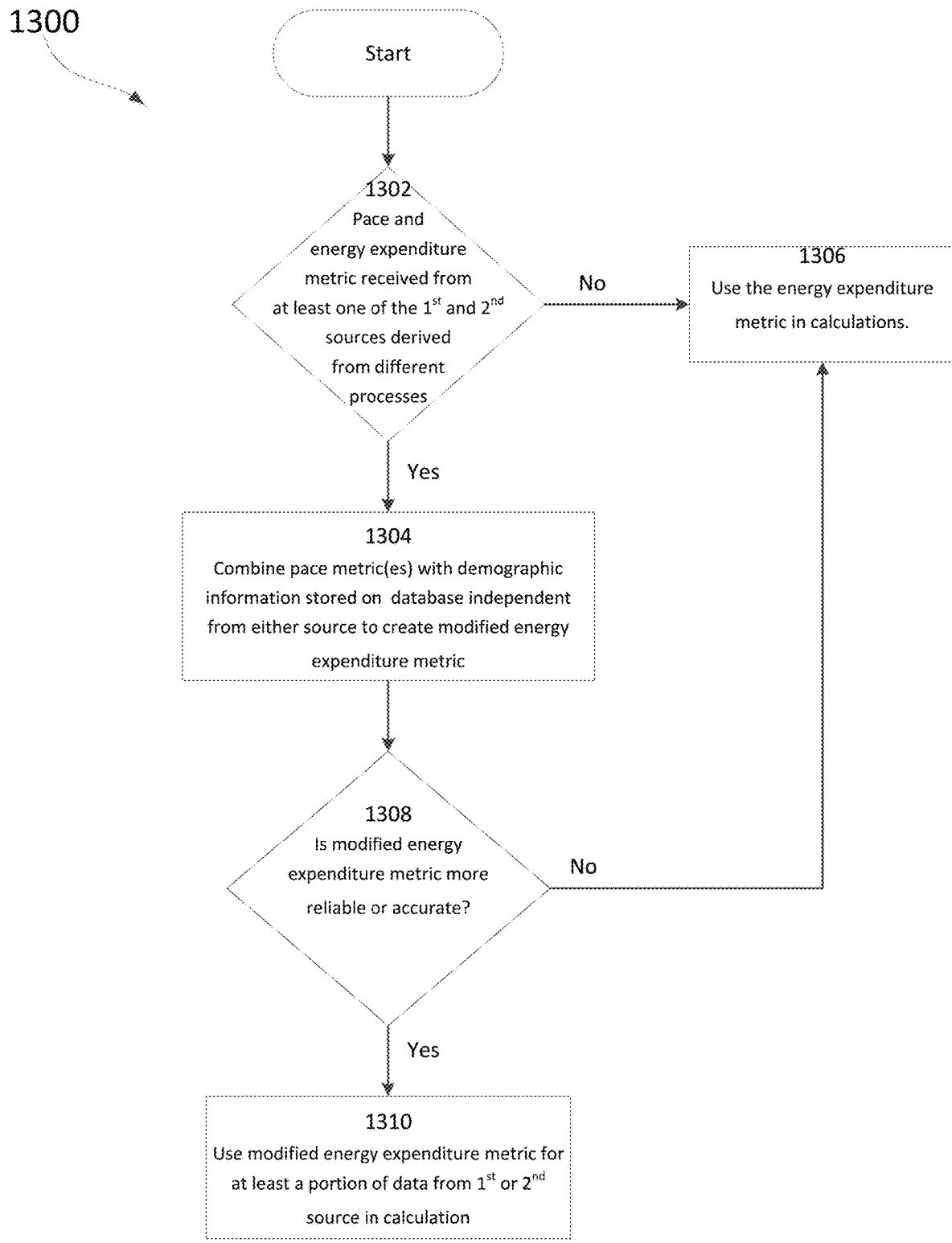
FIG. 13 is a flow diagram depicting an example implementation of utilizing two different metrics derived from different processes at different sources.

FIG. 8A illustrates an example flow diagram 800 which may be used in calculating a combined energy expenditure estimate for a user 124 based on energy expenditure estimates obtained by two or more different devices, which may entirely different devices incapable of communicating with each other, either directly or indirectly. In accordance with one example embodiment, a 1st athletic metric value may be derived from a first process which may be conducted on a 1st device from 1st source (e.g., block 802). For example, the first process may calculate energy expenditure information associated with a first athletic activity performed by the user 124. The first source may be an electronic storage of data (e.g., non-transitory computer-readable medium) configured to determine values or obtain data from which values may be calculated for a user base. In some cases, the first energy expenditure information may include a first energy expenditure estimate and one or more different time stamps, such as first time stamp associated with a start of a first athletic activity and/or a second time stamp associated with an end of the first athletic activity. The process may calculate the value for the metric based upon a specific process, such as at least a portion of that disclosed by flowchart 600. In yet further embodiments, other metric(s) may be calculated, such as pace, acceleration, either alone and/or as part of, or independently of energy expenditure. (FIG. 13 shows flowchart 1300 providing an example utilization of two or more different metrics). Thus, examples with reference to energy expenditure are merely examples and not intended to limit the scope of this disclosure. In instances where data regarding certain parameters, such as energy expenditure, are obtained from two or more sensors or determined by different mathematical calculations, certain aspects of this disclosure may be implemented to determine a resultant output. In such cases, the combined values may be calculated using one or more of an average, a weighted average or a statistical solution. However, such calculations may not be practical in every situation. As such, another method of combining information gathered using different devices may be desired.

A 2nd athletic metric value that is derived from 2nd process conducted on a 2nd device may be received from a 2nd source. For example, instead of determining energy expenditure using data from the same first collection of sensors used in the first process, a second collection of sensors may have been utilized, and/or a different process may be used to determine the value. For example, a first process may use a data from the same sensors (or portion thereof) to classify the user's athletic movements into an activity type or category, whereas a second process may not classify the movements into a category or type. In one embodiment, the first source may be a database of a user's data collected from their GPS device, whereas the second source may be a second database that collects user data from a tri-axis accelerometer. The first source may have an online user interface that allows the user to log in using first credentials and the second source may have an online user interface that allows the same user to log in using second credentials. Because the first and second source may be competitor services, they may be independent of each other, thus the devices used to collect the data and/or provide the data to the non-transitory database, and/or calculate the metric, may not be configurable to communicate, either directly or indirectly. Thus, the devices may not be able to be directly updated with information from the other source(s).

In certain embodiments, a modification scalar may be applied to at least one of the athletic metric values (e.g., block 806). As discussed above, parameters relating to the user's activity may be captured using sensors, which may be located on one or more devices. The sensors may monitor the user's motion, physiological properties, and/or other parameters. A first sensor may result in more accurate determinations, such as for example, energy expenditure calculations while a user is running and a second sensor may result in more accurate determinations, e.g., energy expenditure calculations, while a user is performing squats. For example, a multi-axis accelerometer and/or force sensor may be more accurate for skateboarding or basketball than GPS would be, and on the flip side, a GPS sensor may be more accurate when measuring a hike than a tri-axis accelerometer. However, a GPS sensor combined with a force sensor still may provide even more precise or accurate results. This is merely one example as to why a scalar may be applied to data. The scalar may be applied based upon known or estimated limitations of the user's equipment, environment, and/or other factors. For example, a run in a populated city like Chicago, New York, or Los Angeles may not be as accurately captured with GPS sensors as if the user was conducting the run in a less populated environment with less building or signal obstruction. Further, in those embodiments in which the user's activity is known, estimated, or inputted, the activity may be used to determine how accurate or precise the resultant data is. Thus, either a predetermined scalar or a variable scalar may be used to augment or adjust data received from at least one source.

One or more normalizing factors configured to normalize data from the 1st and/or 2nd source may be applied (e.g., block 808). In various embodiments of the invention, normalizing factors may be used to calculate an athletic metric, such as a cumulative energy expenditure value, which may be expressed as, for example, caloric expenditure. Based on one or more criterion, such as the classification of the user activity, one or more normalizing factors (or processes utilizing one or more factors) may be determined. For example, in one embodiment, at least one of user's 124 activity may be classified (e.g., such as at blocks 603 and/or 706 of shown in FIGS. 6 and 7, respectively and one or more corresponding normalizing factors applied to the athletic metric. In one example embodiment, normalizing factors may be applied to activity classifications (or other variable(s)) to create a normalized athletic metric, which may allow for an improved comparison of activity levels of athletes and/or may promote collaboration among users, normalize results for competition among users of different capabilities, and otherwise encourage activity. In one embodiment, a normalized energy expenditure value may be calculated using Equation 1 and/or Equation 2, each of which have been disclosed above, and, which may be calculated may be performed at a device that includes sensors that monitor activity and/or at another device that includes a processor, such as a mobile phone (see, e.g., 138) or server (see, e.g., 134).

As shown in equation 2, a scalar may be optionally implemented. The scalar used in equation 2 may, but is not required to be, a whole number, such as 1, 3, 5 or 10. In some embodiments, the scalar is selected so that typical energy expenditure points fall within a desired range. The range of points may be desired for various games or competitions, and/or to provide a relation to a virtual currency or point system. Different and varying equations may be selected for different games, activities, population dynamics, and competitions. In one example a group may set handicaps among the players based on fitness, so that NEEVs may only be generated for those athletes that do a common activity or set of activities for longer period(s) of time. A group of users participating in an energy expenditure point competition may agree on a particular equation or method before beginning the competition. Yet, in other embodiments, NEEV calculation may not be explicitly disclosed to one or more athletes or users so as to prevent or attempt to prevent athletes from attempting to maximize points or otherwise "earn" values from conducting activities that exploit one or more imprecisions in the system. As those skilled in the art will appreciate, every model will have limitations. And in this regard, aspects of this innovation attempt to minimize inaccurate and/or imprecise data values via one or more systems and methods disclosed herein. In some embodiments of the invention, a user may participate in multiple competitions and earn different values for the same activity because of different calculation methods. For example, a user may be participating in two competitions that have unique calculation methods. The user may earn two different point totals for the two different games and a third point total for their overall energy expenditure. Some point totals may be maintained separate from an overall point total.

In those embodiments in which the athletic metric relates to energy expenditure in which METs are utilized, some activities, games and/or competitions may limit awarding energy expenditure points for activities that have relatively low MET values. In some embodiments, awarding energy expenditure points for activities that have relatively low MET values may also be limited all of the time or in other situations. An optional step may be added to the process shown in FIG. 8 or other implementations to not award points for activities that do not exceed a MET threshold value. For example, an exemplary threshold value may be 1.0, 2.0 or 3.0. In another embodiment, the threshold value may equal 2.8. Different games and competitions may use other threshold values. When the MET value does not exceed the threshold, a step may be implemented to disregard the corresponding activity and not use the activity when calculating energy expenditure points.

Another embodiment could have the threshold generally applied, but not when games or competitions are underway or at least certain games or competitions. The games or competitions may be based on all values. In another embodiment, a threshold may always apply even to games and competitions. In another embodiment, different thresholds may apply by activity, game and/or competition, e.g., one for running briskly, one for running, one for walking, and a default.

In certain implementations, such as after at least one of user's 124 activity is classified according to one embodiment, one or more processes may be implemented to determine a corresponding MET value. For example, the MET value may correspond to brisk running, running at a moderate pace, walking slowly or any other activity found in conventional MET tables. If an activity was not classified, such as in block 603 and/or 706 of FIGS. 6-7, respectively, a default MET value may be selected or derived. In some embodiment multiple default MET values may be utilized. An activity's intensity, duration or other characteristic(s) may be assessed, from which one or more default METs may be applied. These plural METs may be set via medians/averages, ranges, or other statistical approaches.

If the user's movement does not match an exercise defined by a MET table, the system 100 may identify one or more exercises that include movements similar to the movement being performed by the user. For example, system 100 may determine that the user's lower body moves similar to a squat and upper body moves similar to a pushup. System 100 may calculate the number of calories the user would burn using the identified MET tables as if the users were doing a squat, and as if they were doing a pushup, as approximations for the amount of calories burned by the user. In further embodiments, a new entry may be created. In this regard, certain embodiments may permit the entry and later identification of new movements and/or exercises. In certain embodiments, the user may provide inputs regarding an approximate caloric expenditure for an unidentified movement/exercise. Yet in other embodiments, system 100 may calculate caloric expenditure, such as from one or more sensors as discussed herein. In still yet further embodiments, system 100 may utilize one or more sensor readings as well as an input from a user (and/or third-party) in determining attributes, such as caloric expenditure, for previously unknown movements or exercises. Examples of estimating caloric expenditure without MET tables, may include but are not limited to, determining changes in potential energy.

Alternative embodiments may use alternative or additional equations for calculating point values and/or other quantities (e.g., part of block(s) 808 or 810). The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity values or normalized energy expenditure values and/or steps. Calculating values that are functions of activity values or NEEVs and other variables may be used to compare the efficiencies of various activities. For example, an equation may be used to determine that taking steps at a faster pace may result in activity values or NEEVS accumulating at a faster per step pace. Another exemplary equation may determine activity values or NEEVs per a predetermined distance or a unit of distance.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity values or NEEVs may be displayed to a user via display 235 or a display that is part of a mobile device.

Before, during and/or after the normalized values are calculated, the calculated values (raw, processed, or NEEVs) may be combined, such as being added, to a form a cumulative value (e.g., block 810, which may calculate final cumulative normalized athletic metric for a first time frame). The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the values earned for each activity may be a function of a corresponding activity factor.

Figure 8B:
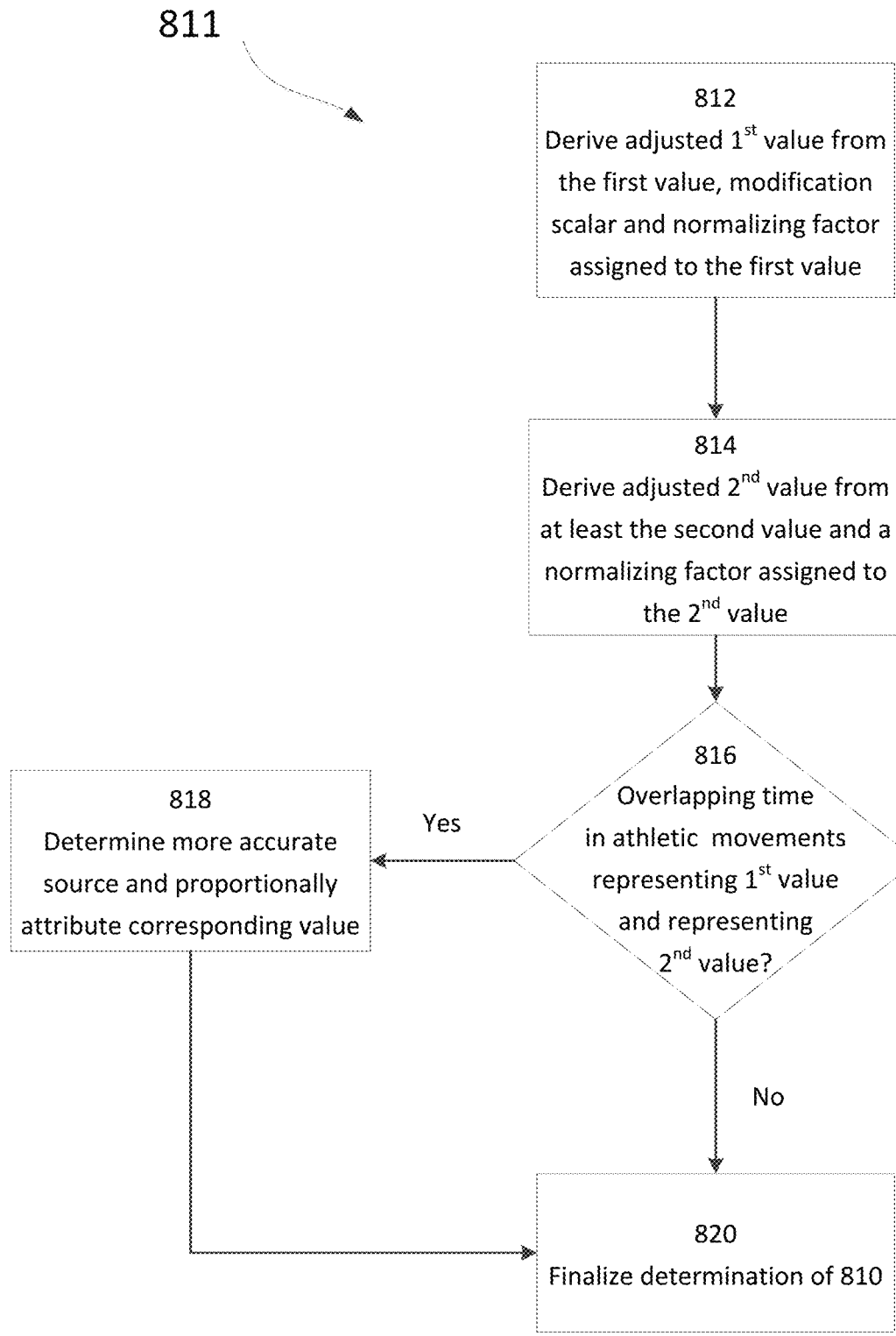
FIG. 8B shows a flow diagram of calculating a cumulative normalized athletic metric in accordance with one embodiment.

FIG. 8B shows flowchart 811 of an example embodiment of calculating a cumulative normalized athletic metric for a first time frame. For example, all or part of flowchart 811 of FIG. 8B may be performed as part of block 810 of flowchart 800 (FIG. 8A). In one embodiment, an adjusted $1^{st}$ value may be derived from the first value; a modification scalar and a normalizing factor assigned to the first value (e.g., block 812). An adjusted $2^{nd}$ value may be derived from at least the second value (e.g., block 814) and a normalizing factor assigned to the $2^{nd}$ value. Those skilled in the art will appreciate that these are merely examples.

Certain embodiments may determine whether there is overlapping time in athletic movements representing the $1^{st}$ value and the $2^{nd}$ value (e.g., block 816). For example, as alluded to above, a collection of sensors may be one or more devices, which in turn, may individually aggregate energy expenditure information. For example, a user may use sensors from two or more different vendors, where a first set of sensors may be configured to synchronize energy expenditure information with a first device and a second set of sensors may be configured to synchronize energy expenditure information with a second device. In such cases, the energy expenditure information may be totaled separately on the different devices. For example, the first device may store a total energy expenditure estimate of 5000 units gathered using the first set of sensors and the second device may store a total energy expenditure estimate of 6000 units gathered using the second set of sensors during the same or at least a portion of the same time. Unlike prior art methods and systems, certain embodiments, may not merely use a default or the highest value. If it is determined that there is overlap, one or more blocks may be implemented to determine or select the more accurate source and proportionally attribute corresponding value (e.g., block 818). Example systems may utilize one or more of the teachings of block 920 of FIG. 9, block 1120 of FIG. 11, and/or other teachings herein.

In one embodiment, calculations may use the user's historical data, other user's historical data, and other sensory data (which may not be available to each other). For example, the second source may provide GPS data which is not available to the first source or otherwise accounted for in the $1^{st}$ source's data. Weather data may further be utilized, such as to provide confirmation or strength in the determination process that the weather could have impacted GPS reception. Battery life may also alter the device(s) accuracy, therefore, may be an attribute considered which value is likely to be more accurate. However, unlike prior art systems and methods any determination may be conducted after a source and/or activity scalar is applied (e.g., scalar from block 806). The process may occur after application of a normalizing factor to the sources under consideration. Thus, in certain embodiments, the adjusted values under consideration may be normalized and scaled before block 818. As shown by way of block 820, the determination of 810 may be finalized using the proportional data for the overlapping time period. In certain embodiments, the final calculations, e.g., a cumulative metric value, does not alter the values obtained to create or generate the cumulative metric. For example, a user's data at the first and/or second source remains unaltered an intact. However, the cumulative data can track a plurality of different disparate data sources.

Figure 9:
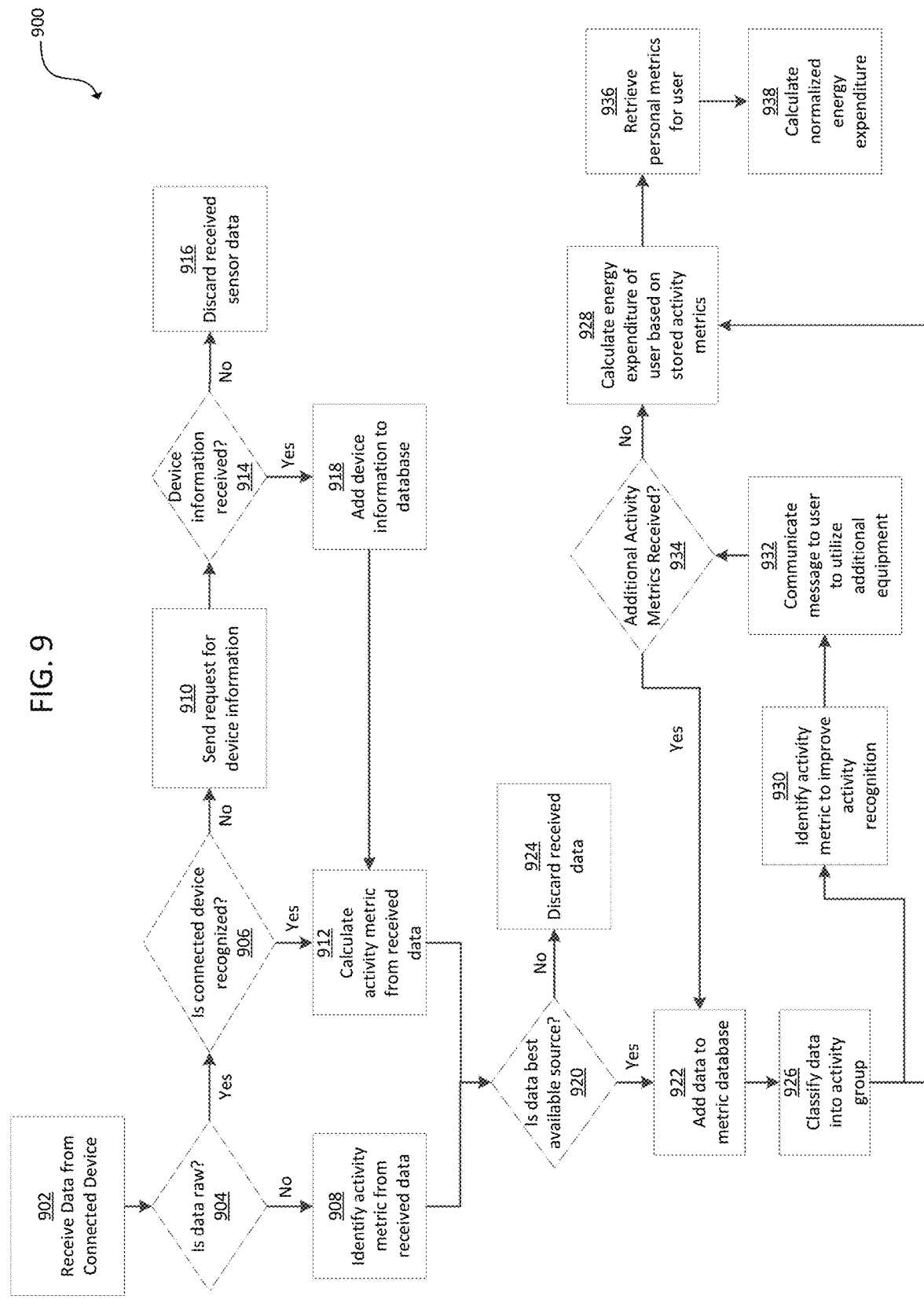
FIG. 9 schematically-depicts one implementation of a process for calculating an energy expenditure of a user from data received from one or more sources.

FIG. 9 schematically-depicts one implementation of a process for calculating energy expenditure for a user from data received from one or more sources. As such, in one example, flowchart 900 of FIG. 9 schematically-depicts a process for calculating an energy expenditure of a user from data received from one or more devices utilizing different operating protocols. In one implementation, a first device may receive sensor data from a second connected device. As such, those of ordinary skill in the art will recognize that any connection hardware, firmware, and/or software utilizing any communication protocol may be utilized to communicate information between the first device and the second device. In one example, the first device may be similar to one or more of devices 112, 126, 128, 130, and/or 400, as previously described. Furthermore, the second connected device may comprise one or more of devices 112, 126, 128, 130, and/or 400, and such that the second connected device may utilize a different operating protocol to the first device. Further details of different operating protocols are described in relation to FIG. 6. Accordingly, in one example, the first device may receive data from the second connected device at block 902 of flowchart 900.

In one example, one or more processes may be executed to determine whether received sensor data comprises of raw sensor data. In particular, raw sensor data may comprise unprocessed, or partially processed, output values from one or more sensor devices. In one implementation, raw sensor data may comprise numerical values generated by one or more sensors from, among others, an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In particular, raw sensor data may be utilized to calculate one or more activity metrics, and such that one or more additional processes may be executed on raw data to arrive at one or more activity metrics, including, but not limited to, energy expenditure, speed, distance, pace, power, and/or others. In one example, one or more processes may be executed to determine whether received sensor data comprises raw sensor data at decision block 904.

In one example, if received sensor data is determined to comprise raw sensor data, flowchart 900 proceeds to decision block 906, wherein one or more processes may be executed to determine whether the connected device is recognized. In particular, and as previously described, flowchart 900 may be executed by a first device using data received from a second connected device. In one implementation, the data received from the second connected device may include information identifying the second connected device. As such, those of ordinary skill in the art will recognize various identification methodologies that may be utilized in this regard. For example, data packet headers may include one or more unique identification codes identifying the second connected device, and the like. As such, in one example, upon receipt of data from the second connected device, one or more processes may be executed to determine whether the second connected device is known to the first device. In one example, these one or more processes executed to determine whether the second connected device is recognized may search through a database of devices with which the first device has communicated previously. As such, those of ordinary skill in the art will recognize various database configurations that may be utilized to store information related to recognized devices. In one example, server 111 may be utilized to store a database of such recognized devices, among others.

In one implementation, if, at decision block 904, the received data is not determined to contain raw data, flowchart 900 proceeds to block 908. Accordingly, in one example, one or more processes may be executed to identify or more activity metrics from received data. In this way, the received data may contain previously-processed information, such that the received data comprises one or more activity metrics including, but not limited to, energy expenditure, speed, distance, pace, power, and/or others.

Turning again to decision block 906, if, in one example, a connected device is not recognized, flowchart 900 proceeds to block 910, wherein a request may be sent from the first device to a second connected device for device information. As such, in one example, this request for device information may comprise a request for a unique identifier of the second connected device, and/or a network address of the second connected device, among others. If, however, the connected device is recognized, flowchart 900 may proceed to block 912, wherein one or more activity metrics may be calculated from the received data. As such, the one or more activity metrics may be calculated based upon information stored in the database related to the second connected device. For example, if it is determined that the second connected device comprises an accelerometer, the raw data received may be identified as acceleration data, and utilized to calculate one or more activity metrics appropriate for data received from an accelerometer. As such, the database of device information may include formulae to be used to calculate one or more activity metrics based upon specific characteristics of a given monitoring device/sensor device. These specific characteristics may include one or more accuracy metrics associated with a given device, or one or more characteristics of an operating protocol/manufacturer associated with a given device. Furthermore, those of ordinary skill in the art will recognize various activity metrics that may be calculated from various raw data types, without departing from the scope of the disclosures described herein. In another example, raw data from multiple different sources may be needed to calculate a given activity metric, among others. Accordingly, an activity metric, such as including, but not limited to, energy expenditure, speed, distance, pace, power, and/or others, may be calculated at block 912 of flowchart 900.

In one example, in response to a request for device information, flowchart 900 may proceed to decision block 914. As such, in one implementation, if no device information is received in response to that request communicated at block 910, flowchart 900 may proceed to block 916, and the received sensor data may be discarded. If, however, device information is received in response to the request made at block 910, flowchart 900 may proceed to block 918, and the requested device information may be added to the device database described in relation to decision block 906.

In one example, flowchart 900 may execute one or more processes to determine whether an activity metric from a given source (i.e. a given second connected device) represents a best available source for said specific activity metric. For example, a user may be utilizing one or more activity devices that may be capable of calculating a given activity metric from separate data sources (i.e. separate sensor devices). As such, in one implementation, flowchart 900 may execute one or more processes to determine a best available source of a given activity metric. In one implementation, one or more processes may be executed to compare a received activity metric to a database of activity metrics stored for a given user. Those of ordinary skill in the art will recognize various different database methodologies that may be utilized to store activity metrics for a user during a given activity period without departing from the scope of the disclosures described herein. As such, decision block 920 may receive an activity metric, and search for the same activity metric within an activity metric database. If it is determined that the activity metric is not already stored within the database, decision block 920 may proceed to block 922 and add the metric to the database. Similarly, if it is determined that the activity metric has already been stored within the database, but that activity metric stored within the database was calculated using data from a less reliable/less accurate source, flowchart 900 may proceed to block 922, and replace the stored activity metric with the newly received activity metric from a better source. If, however, at decision block 920 it is determined that the activity metric is not associated with a best available source, flowchart 900 may proceed to block 924, and discard the received data.

In response to the addition of the activity metric to the activity metric database, flowchart 900 may proceed to block 926, and classify the data into an activity group. As such, in one example, based upon one or more stored activity metrics, an activity being performed by a user may be categorized into a group of activities potentially being performed by the user. As such, this activity group may be a generalized classification comprising one or more activities that a user may be participating in. For example, an activity group may comprise one or more activities classified based upon a speed detected for a user (e.g. a high-speed activity metric may result in an activity group comprising cycling or sprinting, among others).

In one implementation, flowchart 900 may proceed to block 928 and calculate an energy expenditure of the user based on one or more stored activity metrics, and without identifying a specific activity being performed by a user. In particular, having classified received data into an activity group at block 926, flowchart 900 may proceed to block 928 and execute one or more processes to retrieve one or more formulae that may be utilized to calculate an energy expenditure, based upon one or more of the stored activity metrics. In another implementation, an energy expenditure of the user may be calculated following further activity recognition processes. In particular, flowchart 900 may proceed from block 926 to block 930 and identify an activity metric not already stored in a metric database that would improve activity recognition (i.e. reduce a number of activities within the classified activity group from block 926. In one specific example, block 930 may execute one or more processes to identify activity recognition equipment/devices known to be available to a user (e.g. activity devices owned by a user) that may be utilized to update one or more additional activity metrics not currently stored in a metric database for the user for a given activity period.

In one example, flowchart 900 may communicate a message to a user to utilize additional activity recognition equipment in order to improve activity recognition. As such, this message may be communicated to the user at block 932. In one example, the message may inform a user that activity recognition equipment previously known to be in the possession of the user may be utilized to improve recognition of an activity currently being participated in by the user. In response, the user may activate one or more of the recommended additional activity recognition devices. As such, additional activity metrics may be received. Accordingly, if additional activity metrics are received, flowchart 900 may precede from decision block 934 back to block 922. If, however, no additional activity metric for received at block 934, flowchart 900 may proceed to block 928.

In order to calculate an energy expenditure for a user from one or more activity metrics, one or more personal metrics for the user may be retrieved from a metric database. In one example, a database storing one or more personal metrics for user may be a same database storing one or more activity metrics calculated based upon an activity being performed by a user. However, those of ordinary skill in the art will recognize that separate databases for the personal metrics and the activity metrics may be utilized, without departing from the scope of the disclosures described herein. In one example, one or more personal metrics for a user may be retrieved at block 936, wherein the one or more personal metrics may comprise one or more of sex, weigh, height, age, percent body fat, and/or other demographic or physiological parameters.

A normalized energy expenditure for a user may be calculated based upon one or more personal metrics and one or more activity metrics calculated from data outputted by one or more activity devices. As such, those of ordinary skill in the art will recognize various formulae that may be utilized to calculate an energy expenditure based upon a combination of activity metrics and personal metrics, as previously described. Furthermore, calculation of this normalized energy expenditure may be similar to the normalization processes described in relation to FIGS. 7A and 7B.

Figure 10:
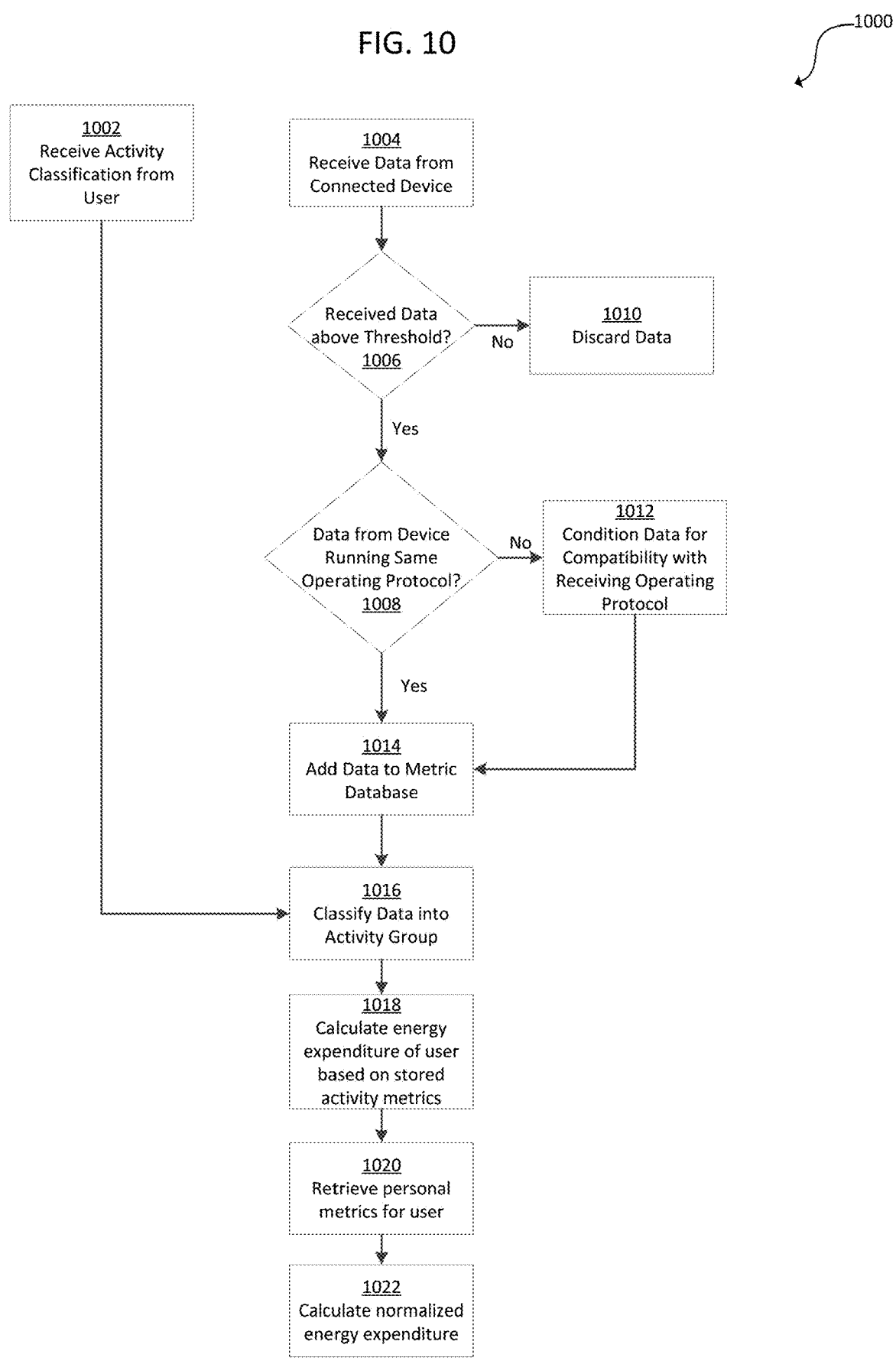
FIG. 10 schematically-depicts another implementation of a process for calculating an energy expenditure of a user from data received from one or more sources.

FIG. 10 schematically-depicts another implementation of a process for calculating an energy expenditure for a user from data received from one or more sources. In one example, FIG. 10 may be utilized to calculate an energy expenditure for a user based upon an activity classification provided by the user. As such, in one example, flowchart 1000 may receive an activity classification from a user at block 1002, and such that the received activity classification includes an identification of an activity currently being performed by a user.

Separate to the activity classification received from the user at block 1002, flowchart 1000 may receive data from a connected device at block 1004. Accordingly, and as previously described in relation to FIG. 9, said connected device may be connected across any network topology/methodology known to those of ordinary skill in the art, without departing from the scope of the disclosures described herein. As such, the connected device may include an activity recognition device having one or more activity sensors, including, among others, an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Furthermore, data received from a connected device may be compared to one or more threshold values to determine whether the received data is suitable for further processing. As such, and at decision block 1006, the received data may be compared to one or more threshold values. If the received data is above the one or more threshold values, flowchart 1000 may proceed to decision block 1008. If however, the received data is not above one or more of the tested threshold values, flowchart 1000 may proceed to block 1010, and the received data may be discarded.

In one implementation, one or more processes may be executed to determine whether the data received at block 1004 has been received from a device utilizing a same operating protocol as a device into which the data was received at block 1004. As such, in one example, one or more processes may determine an operating protocol associated with a device that outputted the received data, at decision block 1008. These one or more processes may identify an operating protocol associated with a device that outputted the received data based upon, in one example, device identification information included in the received data. In one implementation, if it is found that the device that generated the received data utilizes a different operating protocol to the device that received the data, flowchart 1000 may proceed to block 1012. As such, one or more processes may be executed to condition the received data for compatibility with the receiving operating protocol. In this way, one or more processes may be executed to format or augment syntax of received data for compatibility with an operating protocol associated with the receiving device. These one or more processes may be executed at block 1012, and may be similar to one or more conditioning processes discussed in relation to FIG. 6.

In one implementation, data received at block 1004 may comprise one or more activity metrics. As such, and at block 1014 of flowchart 1000, one or more processes may be executed to identify the received activity metrics and add said activity metrics to a database, similar to the activity metric database discussed in relation to FIG. 9. Further, based upon the received activity data, including one or more activity metrics, one or more processes may be executed to classify the received data into an activity group. This classification may be executed at block 1016, or may be similar to those one or more processes executed at block 926 of FIG. 9.

In one implementation, flowchart 1000 may calculate an energy expenditure for a user based upon one or more stored activity metrics. As such, one or more processes may be executed to retrieve the one or more stored activity metrics, in addition to one or more formulae that may be utilized to calculate an energy expenditure based upon the available activity metric information. As such, calculation of an energy expenditure of the user based upon stored activity metrics may be executed at block 1018, and may be similar to block 928 from FIG. 9.

In order to calculate a normalized energy expenditure for a user, as described in relation to FIGS. 7A and 7B, flowchart 1000 may retrieve one or more personal metrics for a user that are stored in a metric database. As such, these personal metrics may include a user sex, weigh, height, age, percent body fat, and/or other demographic or physiological parameters. This retrieval of one or more personal metrics may be executed at block 1020, and may be similar to block 936 from FIG. 9. Accordingly, process 1000 may calculate a normalized energy expenditure at block 1022. In one example, the calculation of a normalized energy expenditure at block 1022 may be similar to those processes executed at block 938 of FIG. 9.

Figure 11:
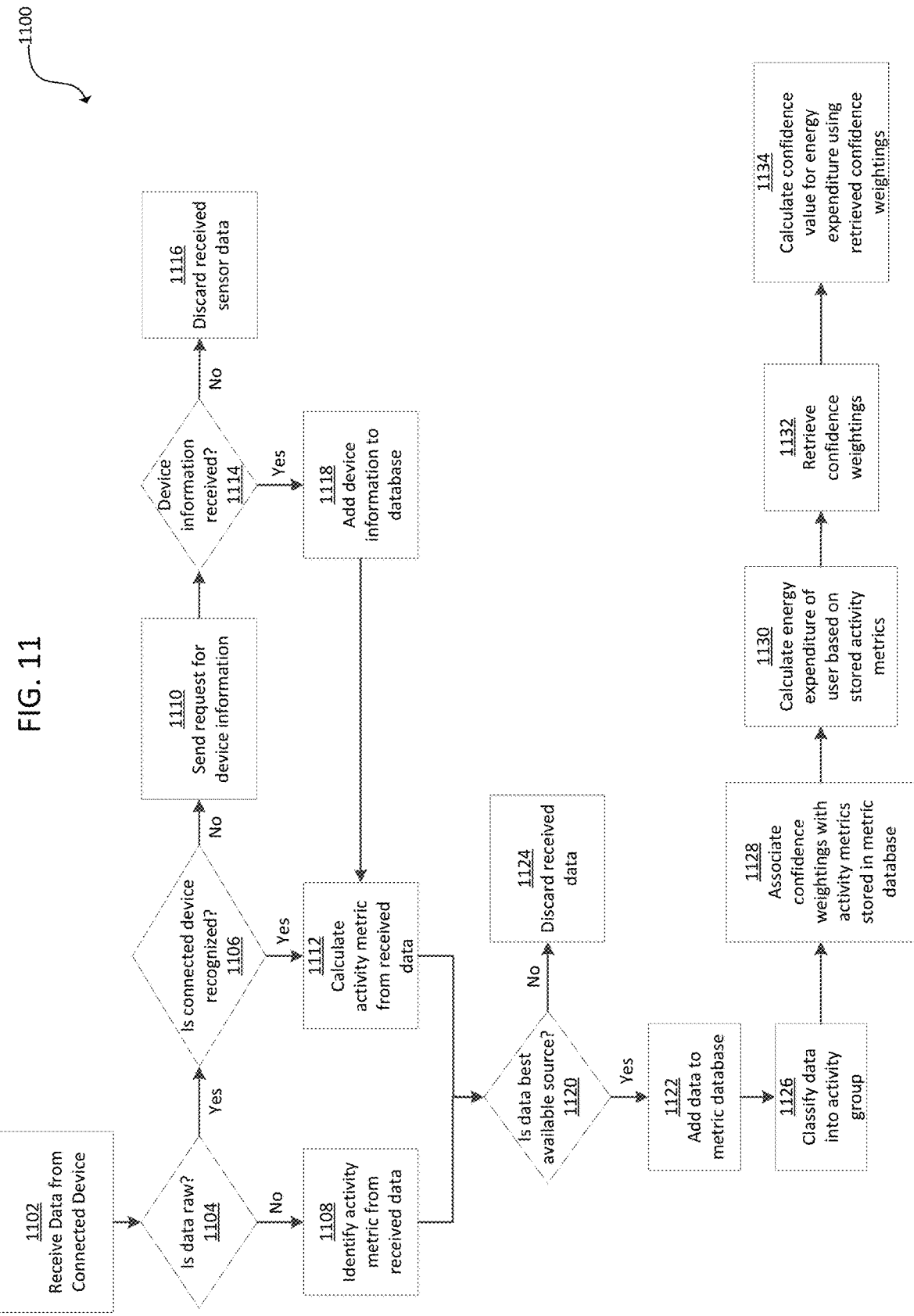
FIG. 11 schematically-depicts an implementation of a process for calculation of a confidence value to be associated with a calculated energy expenditure value.

FIG. 11 schematically-depicts another implementation of a process for calculation of an energy expenditure value for a user based upon received sensor data, as well as calculation of a confidence value to be associated with a calculated energy expenditure. Accordingly, in one implementation, flowchart 1100 may receive data from a connected device at block 1102, and similar to block 902 from FIG. 9. In response, flowchart 1100 may execute one or more processes to determine whether the received data comprises raw data. In one implementation, these one or more processes may be executed at decision block 1104, similar to block 904 from FIG. 9. If it is determined that the received data comprises raw data, flowchart 1100 may proceed to decision block 1106, and one or more processes may be executed to determine whether the connected device is recognized by the receiving device. These one or more processes executed to determine whether the connected device is recognized by the receiving device may be similar to those processes executed at decision block 906 of FIG. 9.

If, in response to those processes executed at decision block 1104, it is determined that the received data does not contain raw data, one or more further processes may be executed to identify one or more activity metrics from the received data. These activity metric recognition processes may be executed at block 1108, and may be similar to those processes executed at block 908 of FIG. 9.

Turning again to decision block 1106, if those processes executed at decision block 1106 determine that the connected device is not recognized, flowchart 1100 may proceed to block 1110. Accordingly, one or more processes may be executed to send a request to the connected device for device information at block 1110. As such, block 1110 may be similar to block 910 from FIG. 9. If, however, the connected device is recognized at decision block 1106, flowchart 1100 may proceed to block 1112, and calculate an activity metric from the received data. In this way, block 1112 may be similar to block 912 from FIG. 9.

If, in response to the request for device information communicated at block 1110, device information is received from the connected device, flowchart 1110 may proceed from decision block 1114 to block 1118. As such, received device information may be added to a database at block 1118. If, however, no device information is received in response to the request is communicated at block 1110, the received sensor data may be discarded at block 1116. In this way, decision block 1114 may be similar to block 914 from FIG. 9, and blocks 1116 and 1180 may be similar to blocks 916 and 918 from FIG. 9.

Decision block 1120 may execute one or more processes to determine whether one or more activity metrics received from a connected device at block 1102 represents one or more best available sources of said activity metrics. In this way, decision block 1120 may be similar to decision block 920 from FIG. 9. In turn, if it is determined that the received activity metrics do not represent a best available source of data, flowchart 1100 may proceed to block 1124, and that the received data may be discarded. Conversely, if the one or more processes executed at decision block 1120 determine that the received activity metrics represent a best available data source, flowchart 1100 may proceed to block 1122, and add the data to a metric database. In this way, block 1122 may be similar to block 922 from FIG. 9. Furthermore, the received data may be classified into an activity group, and such that an activity group may represent one or more activities that may be associated with the data received at block 1102. This classification of data into an activity group may be executed at block 1126, and may be similar to those processes executed at block 926 of FIG. 9.

In one implementation, a confidence weighting may be associated with an activity metric stored in a metric database. As such, a confidence weighting may comprise a numerical value representing an accuracy associated with one or more activity metrics. In one example, a confidence weighting may be based upon a source of data used to calculate a given activity metric. For example, a specific activity metric may be calculated from sensor data received from multiple different sensor types, and such that a first sensor type may output data that is more accurate than a second sensor type. In turn, the specific activity metric may be more accurate when calculated from data outputted from the first sensor type than data outputted from the second sensor type, and the like. In this way, a confidence weighting may be associated with an activity metric based upon one or more source devices from which data was received in order to calculate said activity metric.

In another example, a confidence weighting may be based upon a specific activity being performed by a user. For example, an activity metric may comprise an energy expenditure value associated with the user. However, a confidence weighting associated with this energy expenditure activity metric may take into account a specific activity being performed by a user. For example, if one or more activity recognition processes determine that the user is cycling, a first confidence weighting may be associated with the activity metric. If, however, the one or more activity recognition processes determine that the user is running, a second confidence weighting may be associated with the activity metric. In particular, the first confidence weighting may take into account that an energy expenditure calculated for cycling is likely to be less accurate, given a specific activity recognition device, than the energy expenditure calculated for running, given the same activity recognition device. In one implementation, a confidence weighting may be associated with an activity metric stored in the metric database at block 1128. In yet another example, a confidence weighting may take into account one or more environmental conditions associated with a calculated activity metric. As such, environmental conditions may include a signal-to-noise ratio associated with received sensor data, among others.

In one example, one or more processes to be executed to calculate an energy expenditure of the user from one or more stored activity metrics, and such that the one or more stored activity metrics they comprise one or more of a speed, a pace, an incline on which a user is moving, a heart rate, a metabolic equivalent value, a calorie consumption value, a volume of oxygen consumption, or a power value, among others. In this way, an energy expenditure value may be calculated using one or more formulae specific to a recognized activity and/or activity group within which it is determined that the user is participating. As such, in one example, the calculation of an energy expenditure for a user based upon one or more stored activity metrics may be executed at block 1130 of flowchart 1100.

In one implementation, one or more processes may be executed to retrieve one or more confidence weightings associated with the activity metrics utilized in the calculation of the energy expenditure. In this way, one or more confidence weightings based on, among others, a source of the data received at block 1102, an activity/activity group identified at block 1126, and/or one or more environmental conditions may be retrieved from a database, such as that database described in relation to block 1128. In one example, retrieval of the one or more confidence weightings may be executed at block 1132. Accordingly, in one example, one or more processes may be executed to calculate a confidence value for the calculated energy expenditure for a user, and based upon the retrieved confidence weightings, which are in turn related to the activity metrics utilized in the calculation of the energy expenditure. Those of ordinary skill in the art will recognize various formulae that may be utilized to calculate the confidence value associated with the calculator energy expenditure, without departing from the scope of the disclosures described herein. As such, in one example, the one or more processes executed to calculate the confidence value may be associated with block 1134.

Figure 12:
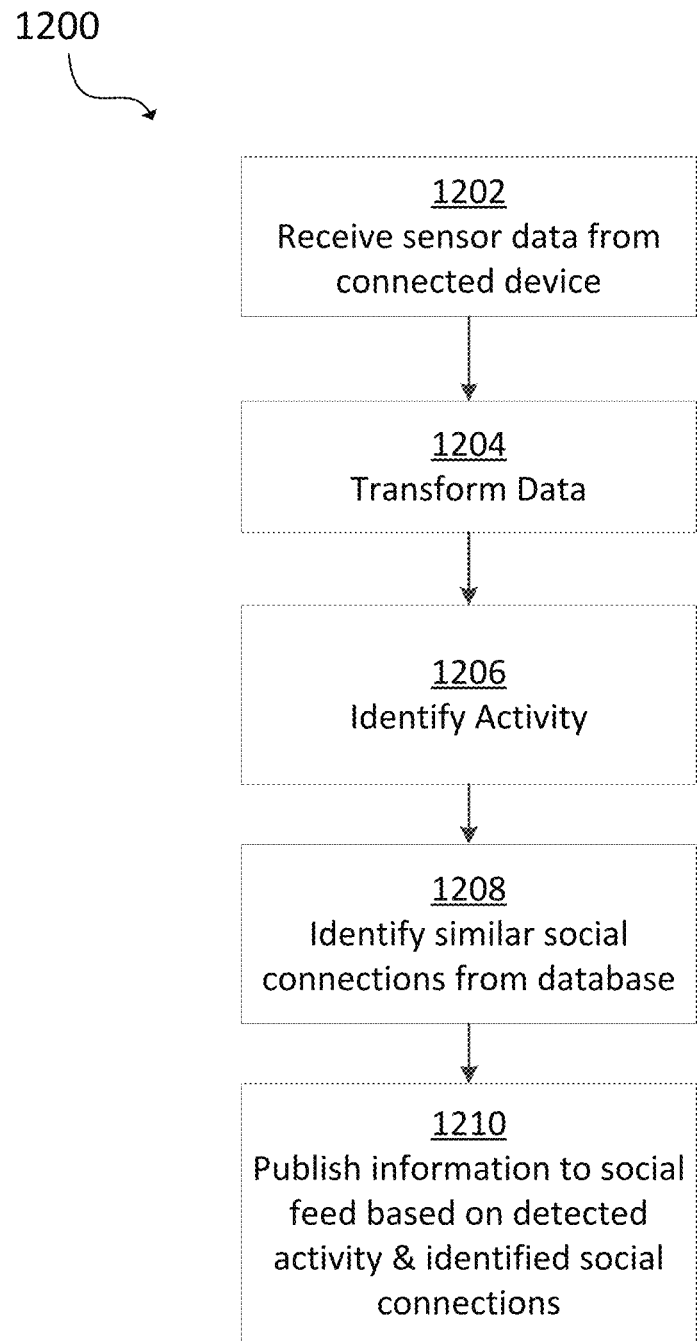
FIG. 12 is a flowchart diagram of a process for publishing activity information to a social feed.

FIG. 12 is a flowchart diagram of a process for publishing activity information to a social feed. In particular, flowchart 1200 may receive sensor data from a connected device. In this way, flowchart 1200 may be executed by a first device utilizing a first operating protocol, and such that the first device is in communication with a second device utilizing a second operating protocol. As such, in one example, sensor data may be received from the connected device at block 1202 of flowchart 1200, and such that blocks 1202 may be similar to block 1102 from FIG. 11.

In one implementation, one or more processes may be executed to transform data received from the connected device. As such, these one or more processes may transform the received data to extract one or more activity metrics, and the like. In one example, received data may comprise raw data from which one or more activity metrics may be calculated. In another example, the received data may comprise pre-processed information that may be interpreted as one or more activity metrics. As such, these activity metrics may include, among others, speed, a pace, an incline on which a user is moving, a heart rate, a metabolic equivalent value, a calorie consumption value, a volume of oxygen consumption, or a power value. In one implementation, the received data may be transformed at block 1204.

In one example, flowchart 1200 may identify one or more activities associated with the received sensor data. As such, in one implementation, an activity associated with the received sensor data may be identified based upon one or more activity recognition processes executed on received sensor data, or based upon an explicit identification of an activity communicated within the received sensor data (e.g. an activity identifier communicated within the received sensor data). As such, those of ordinary skill in the art will recognize various activity recognition processes that may be utilized in this regard, without departing from the scope of the disclosures described herein. Further, in one example, identification of one or more activities associated with received sensor data may be executed at block 1206 of flowchart 1200.

In one example, flowchart 1200 may identify one or more social connections from a database, based upon the received sensor data and the one or more identified activities. As such, the one or more social connections may be associated with one or more social networks. In particular, the one or more social networks may include groups of individuals with common interests (e.g. athletic activity interests, and the like). Further, the database from which the one or more social connections may be identified may be stored locally, such as one or more of devices 112, 126, 128, 130, and/or 400, or may be a remote database stored in a remote server, such as server 111, and the like. In this way, one or more processes may be executed to identify one or more social connections based upon one or more specific activities being performed by the user. Accordingly, these one or more identification processes may be executed at block 1208 of flowchart 1200.

In one example, a data feed, otherwise referred to as a feed, an electronic message board, or communication channel may be utilized by a user in order to communicate information related to an activity being performed by a user. As such, in one implementation, the data feed may communicate athletic performance information to one or more social connections associated with user. In this way, a user may communicate real-time information related to an activity being performed by the user, and such that said one or more social connections may compare their own athletic performances to a real-time performance associated with the user. In one example, one or more processes may publish athletic performance information to a social feed associated with user, based upon the detected activity associated with block 1206, and the social connections identified at block 1208. In one example, this publication may be executed at block 1210.

FIG. 13 is flowchart 1300 which shows an example implementation of utilizing two different metrics from two different sources that were derived from two different processes. For example, in example decision 1302, it may be determined whether a first metric (e.g., pace and/or energy expenditure metric) obtained from a first source (such as the $1^{st}$ source of block 802 of FIG. 8A) and a metric (e.g., energy expenditure and/or pace metric) obtained from a second source (such as the $2^{nd}$ source of block 804 of FIG. 8B). In one embodiment, pace may be provided from the first source and the second source. In one embodiment, the energy expenditure metric from multiple sources may be provided from the same or similar processes (which may be separate from the calculation of pace). The first source may utilize a first process comprising receiving locational data of the athlete during at least a portion of the first time frame, and based upon the locational data, determining a pace of the athlete during relevant portion of the first time frame. The second source may utilize a second process comprising determining a quantity of steps taken by the athlete during at least a portion of the first time frame and based upon at least the quantity of steps determined, determining a pace of the athlete during the relevant portion of the first time frame.

Despite the $1^{st}$ and $2^{nd}$ sources being independent from each other and not having access to each other's data, certain embodiments may utilize either source's data and/or additional data. For example, in one embodiment a pace metric may be combined with demographic information stored on a database independent from either source to create a modified energy expenditure metric (e.g., block 1304; if decision 1302 is in the negative, however, block 1306 may be implemented to utilize the energy expenditure metric in calculations. In one embodiment, a pace metric received from both of the first and second sources is combined with demographic information located in a central database that is independent from the first and second source to create a modified energy expenditure metric.

In certain embodiments, the combination of the pace metrics with the demographic information is part of the modification of the first process value from the value calculated from the first process based upon the identity of at least one of the first source and the first device.

Block 1308 may be implemented to determine whether the modified energy expenditure metric (e.g., determined at block 1304) or the received energy expenditure more reliable or accurate. If it is, block 1310 may be implemented in which the modified energy expenditure metric may be used for at least a portion of data from $1^{st}$ or $2^{nd}$ source in calculation. If not, block 1306 may be implemented to use the energy expenditure metric for at least portion of data from $1^{st}$ or $2^{nd}$ source in subsequent calculations.

For the avoidance of doubt, the present application extends to the subject-matter described in the following numbered paragraphs (referred to as "Para" or "Paras"):

1. A non-transitory computer-readable medium comprising computer-executable instructions that when executed by a processor are configured to perform at least:
   receiving data from a connected device, wherein the connected device utilizes a first operating system and the processor utilizes a second operating system;
   identifying an activity metric associated with the received data;
   storing the received data in the metric database;

classifying the received data into an activity group;
associating one or more stored activity metrics with one or more respective confidence weightings, based on the classified activity group;
calculating an energy expenditure value of a user from the one or more stored activity metrics; and
calculating a confidence value to be associated with the energy expenditure value, based on the one or more confidence weightings.

2. The non-transitory computer-readable medium of Para 1, further comprising, prior to storing the received data in the metric database:
determining, by comparing the received data to a metric database, whether the received data is a best available source of data for the activity metric,
wherein if the received data is not a best available source of data for the activity metric, discarding the received data.

3. The non-transitory computer-readable medium of Para 1 or 2, wherein the confidence value represents an accuracy of the calculated energy expenditure value.

4. The non-transitory computer-readable medium of any preceding Para, wherein a confidence weighting, from the one or more confidence weightings, is associated with the activity metric based on one or more characteristics of the connected device.

5. The non-transitory computer-readable medium of any preceding Para, wherein a confidence weighting, from the one or more confidence weightings, is associated with the activity metric based on one or more environmental factors.

6. The non-transitory computer-readable medium of Para 5, wherein the one or more environmental factors include a signal to noise ratio of the received data.

7. The non-transitory computer-readable medium of any preceding Para, wherein the received data is raw sensor data.

8. The non-transitory computer-readable medium of Para 7, wherein the activity metric is calculated from the raw sensor data by the processor.

9. The non-transitory computer-readable medium of any preceding of Paras 1 to 6, wherein the received data comprises the activity metric pre-calculated by the connected device.

10. The non-transitory computer-readable medium of any preceding Para, wherein the activity group comprises one or more activities that can be recognized based on one or more activity metrics stored in the metric database.

11. The non-transitory computer-readable medium of Para 10, wherein the computer-executable instructions, when executed by the processor, are further configured to perform:
identifying an additional activity metric, not stored in the metric database, to improve activity recognition by reducing a number of activities in the activity group.

12. The non-transitory computer-readable medium of any preceding Para, wherein in order to calculate the energy expenditure of the user, the processor utilizes personal activity metrics stored in the metric database, including: an age, a weight, a height, and a gender of the user.

13. The non-transitory computer-readable medium of Para 12, wherein the personal activity metrics include a resting heart rate of the user.

14. The non-transitory computer-readable medium of Para 12 or 13, wherein in order to calculate the energy expenditure of the user, the processor further utilizes performance activity metrics that include a time over which an activity is being performed by the user, and at least one performance activity metric selected from: a speed, a gradient, a power, a heart rate, a volume of oxygen consumption, a metabolic equivalent, and a calorie count.

15. The non-transitory computer-readable medium of any of Paras 12 to 14, wherein the computer-executable instructions, when executed by the processor, are further configured to perform:
normalizing the energy expenditure value of the user based on the personal activity metrics.

16. An apparatus comprising:
a processor;
an input interface, configured to receive an activity classification input from a user and sensor data from a connected device, wherein the connected device utilizes a first operating protocol and the input interface utilizes a second operating protocol;
a memory storing computer-readable instructions that, when executed by the processor, cause the apparatus to:
identify, based on the activity classification input from the user, an activity being performed by the user;
identify an activity metric associated with the received sensor data;
storing the received sensor data in the metric database;
classifying the received sensor data into an activity group;
associating one or more activity metrics stored in the metric database with one or more respective confidence weightings, based on the classified activity group;
calculating an energy expenditure of the user from the one or more stored activity metrics; and
calculating a confidence value to be associated with the energy expenditure value, based on the one or more confidence weightings.

17. The apparatus of Para 16, wherein the computer-readable instructions, when executed by the processor, further cause the apparatus to, prior to storing the received sensor data in the metric database:
determine, by comparing the sensor received data to a metric database, whether the received sensor data is a best available source of data for the identified activity metric,
wherein if the received sensor data is not the best available source of data for the identified activity metric, discarding the received sensor data.

18. The apparatus of Para 17, wherein the computer-readable instructions, when executed by the processor, further cause the apparatus to:
determine whether the received data is a best available source of data for the identified activity metric by comparison of the received data to a threshold value.

19. The apparatus of any of Paras 16 to 18, wherein the computer-readable instructions, when executed by the processor, further cause the apparatus to:
condition the received data for compatibility with the second operating protocol.

20. The apparatus of any of Paras 16 to 19, wherein the connected device comprises a sensor selected from the group consisting of a GPS, an accelerometer, a heart rate sensor, and a gyroscope.

21. The apparatus of any of Paras 16 to 20, wherein in order to calculate the energy expenditure of the user, the processor utilizes personal activity metrics stored in the metric database, including: an age, a weight, a height, and a gender of the user.

22. The apparatus of Para 21, wherein the personal activity metrics include a resting heart rate of the user.

23. A computer-implemented method of calculating a final cumulative athletic metric based upon an athlete's athletic movements during a first time frame that comprises at least a first and a second time period, comprising:
receiving from a first source, a first value representing a first athletic metric derived from a first process conducted on a first device;
receiving from a second source that is independent of the first source, a second value representing the first athletic metric derived from a second process conducted on a second device;
based upon an identity of at least one of the first source and the first device, associating a modification scalar to the first value;
assigning a normalizing factor configured to normalize data received from the first source and the second source;
calculating a final cumulative normalized athletic metric for the first time frame using an adjusted first value and adjusted second value, wherein the adjusted first value is derived from the first value, the modification scalar and the assigned normalizing factor, and an adjusted second value is derived from at least the second value and the assigned normalizing factor.

24. The method of Para 23, wherein the normalizing factor and the modification scalar are each applied to the first value.

25. The method of Para 23 or 24, wherein one of the assigned normalizing factor or the modification scalar is directly applied to the first value to provide an interim first value, and the other of the normalizing factor and the modification scalar is applied to the interim first value.

26. The method of any of Paras 23 to 25, further comprising:
determining that the first value represents athletic movements during a first time period within the first time frame and the second value represents athletic movements during a second time period within the first time frame; and
wherein the calculation of the final cumulative normalized athletic metric comprises summing the adjusted first value and the adjusted second value to create the final cumulative normalized athletic metric.

27. The method of any of Paras 23 to 26, wherein the normalizing factor is assigned to the first value based upon the activity being performed by the athlete.

28. The method of any of Paras 23 to 27, further comprising:
determining that the first value represents athletic movements during a first time period within the first time frame and the second value represents athletic movements during a second time period within the first time frame, wherein at least a portion of the first time period and the second time period overlap;
and wherein the calculating the final normalized cumulative athletic metric comprises:
determining that the first source better represents the athletic movements, and in response, proportionally attributing the first value to the overlap.

29. The method of any of Paras 23 to 28, wherein the first athletic metric comprises an energy expenditure metric.

30. The method of any of Paras 23 to 29, wherein the athletic metric comprises a pace metric.

31. The method of Para 30, wherein the first process comprises:
receiving locational data of the athlete during at least a portion of the first time frame; and
based upon the locational data, determining a pace of the athlete during relevant portion of the first time frame; and
wherein the second process comprises:
determining a quantity of steps taken by the athlete during at least a portion of the first time frame; and
based upon at least the quantity of steps determined, determining a pace of the athlete during the relevant portion of the first time frame.

32. The method of Para 30 or 31, further comprising:
combining the pace metric received from both of the first and second sources with demographic information located in a central database that is independent from the first and second source to create an energy expenditure metric.

33. The method of Para 32, wherein the combination of the pace metrics with the demographic information is part of the modification of the first process value from the value calculated from the first process based upon the identity of at least one of the first source and the first device.

34. The method of Para 33, wherein athletic metric comprises both an energy expenditure metric and a pace metric, the method further comprising:
combining the pace metric received from both of the first and second sources with demographic information stored on a central database that is independent from the first and second source to create a modified energy expenditure metric; and
determining whether to use the energy expenditure metric or the modified energy expenditure.

35. The method of Para 33 or 34, wherein a first time period and a second time period of the first time frame overlap.

CONCLUSION

Aspects of the embodiments have been described in terms of illustrative embodiments thereof. Numerous other embodiments, modifications and variations within the scope and spirit of the appended Clauses will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

We claim:
1. An athletic system comprising:
a processor; a display; and
a non-transitory, computer-readable medium comprising computer-executable instructions that, when executed by the processor, are configured to cause the processor to at least:

receive, from a connected device, athletic, data of a user, the athletic data collected from one or more sensors associated with the connected device, wherein the connected device utilizes a first operating system and the processor utilizes a second operating system;

identify an activity metric associated with the received athletic data;

prior to any classification of the received athletic data into an athletic activity group, determine, by comparing the received athletic data to a metric database, whether the received athletic data is a best available source of data for the activity metric;

based on determining that the received athletic data is not a best available source of data for the activity metric, discard the received athletic data; and based on determining that the received athletic data is the best available source of data for the activity metric:

store, in the metric database, the identified activity metric associated with the received athletic data;

classify the received athletic data into an athletic activity group;

identify an additional activity metric, not stored in the metric database, to improve activity recognition by reducing a number of activities in the athletic activity group;

associate the stored activity metric with a first confidence weighting, of one or more confidence weightings, wherein the first confidence weighting is determined based on a signal to noise ratio associated with received athletic data corresponding to the stored activity metric;

calculate, from the stored activity metric, an energy expenditure value of the user;

calculate, based on the first confidence weighting, a confidence value to be associated with the energy expenditure value; and display the calculated energy expenditure value of the user on the display.

2. The athletic system of claim 1, Further comprising: an input interface configured to receive an activity classification input from the user and sensor data from the connected device.

3. The athletic system of claim 1, wherein the confidence value represents an accuracy of the calculated energy expenditure value.

4. The athletic system of claim 1, wherein a second confidence weighting, from the one or more confidence weightings, is associated with the activity metric, and wherein the second confidence weighting is determined based on one or more environmental factors.

5. The athletic system of claim 1, wherein the received athletic data is raw sensor data.

6. The athletic system of claim 5, wherein the activity metric is calculated from the raw sensor data by the processor.

7. The athletic system of claim 1, wherein the received athletic data comprises the activity metric pre-calculated by the connected device.

8. The athletic system of claim 1, wherein the athletic activity group comprises one or more activities that can be recognized based on one or more activity metrics stored in the metric database.

9. The athletic system of claim 1, wherein calculating the energy expenditure value of the user comprises: processing personal activity metrics stored in the metric database, including at least two of: an age, a weight, a height, and a gender of the user.

10. The athletic system of claim 9, wherein calculating the energy expenditure value of the user comprises: utilizing the personal activity metrics stored in the metric database, wherein the personal activity metrics further include a resting heart rate of the user.

11. The athletic system of claim 9, wherein calculating the energy expenditure value of the user comprises: utilizing performance activity metrics that include a time over which an activity is being performed by the user, and at least one performance activity metric selected from: a speed, a gradient, a power, a heart rate, a volume of oxygen consumption, a metabolic equivalent, and a calorie count.

12. The athletic system of claim 11, wherein the non-transitory, computer-readable medium further comprises computer-executable instructions that, when executed by the processor, are configured to cause the processor to: normalize the energy expenditure value of the user based on the personal activity metrics.

13. A computer-implemented method of calculating a final cumulative athletic metric, based upon athletic movements of an athlete during a first time frame comprising:

electronically receiving, from a first source, a first value representing a first athletic metric derived from first sensor data collected during a first process conducted on a first device;

electronically receiving, from a second source that is independent of the first source, a second value representing the first athletic metric derived from second sensor data collected during a second process, independent of and distinct from the first process, conducted on a second device;

receiving, from at least one of the first source and the second source, information identifying an activity being performed by the athlete during the first time frame;

based on an identity of at least one of the first source and the first device, calculating a modified first value by applying a modification scalar to the first value, wherein the modification scalar corrects for limitations of the first device;

determining, based on the identified activity, a normalizing factor configured to normalize data received from the first source and the second source, wherein the normalizing factor is used to convert a received athletic metric into a normalized athletic metric to allow for comparison of activity levels between different users;

calculating an adjusted first value by applying the normalizing factor to the modified first value;

calculating an adjusted second value by applying the normalizing factor to the second value;

calculating a cumulative normalized athletic metric for the first time frame by adding the adjusted first value and the adjusted second value; and determining that the adjusted first value represents athletic movements during a first time period within the first time frame and the adjusted second value represents athletic movements during a second time period within the first time frame, wherein at least a portion of the first time period and the second time period overlap, wherein the calculating the cumulative normalized athletic metric comprises: determining that the first source better represents the athletic movements, and in response, proportionally attributing the adjusted first value to the overlap;

outputting the cumulative normalized athletic metric for use by the athlete.

14. The method of claim 13, further comprising: determining that the first value represents athletic movements during a first time period within the first time frame and the second value represents athletic movements during a second time period within the first time frame.

15. The method of claim 13, further comprising: determining which of the first source or the second source is a best available source for the first athletic metric; and attributing the data collected during the at least the portion of the time to one of the adjusted first value or the adjusted second value, based on the determined best available source.

16. The method of claim 13, wherein the first device comprises a wrist-worn athletic monitoring device and the second device comprises a sensor on or within a shoe.

\* \* \* \* \*

UNITED STATES PATENT AND TRADEMARK OFFICE
CERTIFICATE OF CORRECTION

PATENT NO. : 10,657,156 B2
APPLICATION NO. : 14/988216
DATED : May 19, 2020
INVENTOR(S) : Andon et al.

It is certified that error appears in the above-identified patent and that said Letters Patent is hereby corrected as shown below:

In the Specification

Column 4, Line 42:
Delete "Playstation" and insert --PlayStation--

Column 13, Line 57:
Delete "training day that" and insert --training data--

Column 14, Line 26:
Delete "sensor aggregated" and insert --sensor are aggregated--

Column 14, Line 47:
Delete "be executed" and insert --to be executed--

Column 17, Line 21:
Delete "a person" and insert --a comparison--

Column 20, Line 10:
Delete "that's the" and insert --that the--

Column 20, Line 13:
Delete "herein, including" and insert --herein.--

Column 20, Line 14:
Delete "in relation to In" and insert --In--

Column 20, Line 47:
Delete "to detected" and insert --to detect--

Signed and Sealed this
Eighteenth Day of August, 2020

Andrei Iancu
*Director of the United States Patent and Trademark Office*

CERTIFICATE OF CORRECTION (continued)
U.S. Pat. No. 10,657,156 B2

Column 20, Line 48:
Delete "such as device" and insert --such a device--

Column 20, Line 50:
Delete "determine" and insert --determining--

Column 35, Line 33:
Delete "Separate to" and insert --Separate from--

Column 38, Line 26:
Delete "to be executed" and insert --may be executed--

Column 38, Line 28:
Delete "and such that the" and insert --such that the--

Column 38, Line 29:
Delete "they comprise" and insert --may comprise--

Column 40, Line 33:
Delete "1304;" and insert --1304)--

In the Claims

Column 45, Line 1:
In Claim 1, delete "athletic," and insert --athletic-- therefor Column 45, Line 39:
In Claim 2, delete "Further" and insert --further-- therefor Column 46, Line 21:
In Claim 13, delete "metric," and insert --metric-- therefor Column 46, Line 54:
In Claim 13, after "value;", delete "and"

Column 46, Line 65:
In Claim 13, after "overlap;", insert --and--